United States Patent
Kim

(10) Patent No.: US 11,583,561 B2
(45) Date of Patent: *Feb. 21, 2023

(54) **COMPOSITION FOR PREVENTING, TREATING, OR ALLEVIATING VIRAL INFECTION DISEASES OR RESPIRATORY DISEASES COMPRISING VESICLE DERIVED FROM *LACTOBACILLUS PARACASEI***

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,347

(22) Filed: Jan. 27, 2022

(65) Prior Publication Data

US 2022/0241356 A1 Aug. 4, 2022

(30) Foreign Application Priority Data

Feb. 1, 2021 (KR) .......................... 10-2021-0014070
Dec. 8, 2021 (KR) .......................... 10-2021-0174687

(51) Int. Cl.
*A61K 35/747* (2015.01)
*A61P 31/12* (2006.01)

(52) U.S. Cl.
CPC ............ *A61K 35/747* (2013.01); *A61P 31/12* (2018.01)

(58) Field of Classification Search
CPC . A61K 35/747; C12N 1/205; C12R 2001/225
See application file for complete search history.

(56) References Cited

U.S. PATENT DOCUMENTS 10,987,386 B2 * 4/2021 Kim .................... A61K 9/007
2018/0055894 A1 * 3/2018 Kim ...................... A61P 11/02

FOREIGN PATENT DOCUMENTS

| KR | 10-1614262 B1 | 4/2016 |
| KR | 10-2020-0053531 A | 5/2020 |
| NO | 2018/220416 A1 | 12/2018 |

OTHER PUBLICATIONS

Zheng et al. "A taxonomic note on the genus *Lactobacillus*: Description of 23 novel genera, emended description of the genus *Lactobacillus* Beijerinck 1901, and union of Lactobacillaceae and Leuconostocaceae" Int. J. Syst. Evol. Microbiol. 2020;70:2782-2858 (Year: 2020).*

Belkacem et al., "Lactobacillus paracasei feeding improves immune control of influenza infection in mice", PLoS ONE, 2017, 12 (9): e0184976.

Choi et al., "Lactobacillus paracasei-derived extracellular vesicles attenuate the intestinal inflammatory response by augmenting the endoplasmic reticulum stress pathway", Experimental & Molecular Medicine, 2020, 52: 423-437.

* cited by examiner

*Primary Examiner* — Thane Underdahl
(74) *Attorney, Agent, or Firm* — Vorys, Sater, Seymour and Pease LLP; Mih Suhn Koh

(57) ABSTRACT

Provided is a method for preventing, alleviating, or treating a viral infectious disease or a respiratory disease, comprising administering a composition containing vesicles derived from *Lactobacillus paracasei* as an active ingredient to a subject in need thereof, wherein the vesicles may be orally administered and delivered to the lung to suppress a respiratory disease, administered to a COVID-19 virus- or influenza virus-infected model to suppress the replication of the COVID-19 virus and clinical symptoms caused by the influenza virus.

5 Claims, 24 Drawing Sheets

*p<0.05; p<0.01; *p<0.001 vs. G1

COMPOSITION FOR PREVENTING, TREATING, OR ALLEVIATING VIRAL INFECTION DISEASES OR RESPIRATORY DISEASES COMPRISING VESICLE DERIVED FROM *LACTOBACILLUS PARACASEI*

TECHNICAL FIELD

The present invention relates to a composition for preventing, treating, or alleviating a viral infectious disease or respiratory disease, comprising vesicles derived from *Lactobacillus paracasei* as an active ingredient, and the like.

This application claims priority to and the benefit of Korean Patent Application Nos. 10-2021-0014070 and 10-2021-0174687 filed in the Korean Intellectual Property Office on Feb. 1, 2021, and Dec. 8, 2021, respectively, and all the contents disclosed in the specification and drawings of the applications are incorporated in this application.

BACKGROUND ART

Viral infectious diseases cause a wide variety of illnesses, and symptoms thereof also vary depending on the type of virus. Examples of viruses that cause respiratory diseases include influenza viruses, coronaviruses, rhinoviruses, and the like, examples of viruses that cause enteritis such as diarrhea include rotaviruses and enteroviruses, examples of viruses that cause immune diseases include retroviruses, and examples of viruses that cause cancer include adenoviruses, papillomaviruses, hepatitis B and C viruses, and the like. Further, herpesviruses may also cause cold sores on the skin of the face or genitals.

As the COVID-19 pandemic has recently become widespread worldwide, respiratory diseases caused by viral infections and complications thereof have become a major problem worldwide. In addition, there is increasing evidence that diseases, thought to be non-infectious diseases in the past, are caused by actual infectious agents, and it has been revealed that *Helicobacter pylori* are a representative cause of gastric cancer, and human papillomaviruses are important causes of cervical cancer. Particularly when the diseases are accompanied by immune dysfunction, complications such as severe pneumonia during infection with COVID-19, influenza, bacteria, and the like cause a fatal outcome, so there is an increasing need for a drug capable of regulating immune dysfunction.

Inflammation is a local or systemic protective mechanism against the damage or infection of cells and tissues, and is typically caused by a cascade of biological reactions occurring as humoral mediators that constitute the immune system directly respond to the damage or infection, or stimulate the local or systemic effector system. Common compositions used to treat or prevent inflammatory diseases are largely classified into steroidal and non-steroidal compositions, most of which are often accompanied by various side effects in many cases.

It is known that the number of microorganisms that coexist in the human body reaches 100 trillion, which is about 10-fold larger than that of human cells, and the number of genes of microorganisms is 100-fold larger than that of humans. A microbiota or microbiome refers to a microbial community including bacteria, archaea and eukarya present in a given habitat.

Bacteria that coexist in our bodies and bacteria that exist in the surrounding environment secrete nanometer-sized vesicles to exchange information such as genes, low molecular compounds, and proteins with other cells. The mucosa forms a physical defense membrane through which particles having a size of 200 nanometers (nm) or more cannot pass so that bacteria coexisting in the mucosa cannot pass through the mucosa, but bacteria-derived extracellular vesicles have a size of approximately 20 to 200 nanometers, and thus relatively freely pass through epithelial cells via the mucosa to be absorbed in our bodies. Although bacteria-derived vesicles are secreted from bacteria, they differ from bacteria in terms of their constituents, absorption rate in the body, and risk of side effects, and therefore, the use of bacteria-derived vesicles is completely different from that of living cells or has a significant effect. Locally secreted bacterial-derived vesicles are absorbed through the epithelial cells of the mucosa to induce a local inflammatory response, and vesicles that have passed through the epithelial cells are systemically absorbed to be distributed to respective organs, and regulate immune and inflammatory responses in the distributed organs. For example, vesicles derived from pathogenic Gram-negative bacteria such as *Escherichia coli* cause a local inflammatory response and cancer, and promote a systemic inflammatory response and blood coagulation through a vascular endothelial cell inflammatory response when absorbed into blood vessels. In addition, such vesicles are absorbed into muscle cells on which insulin acts, and the like to cause insulin resistance and diabetes. In contrast, vesicles derived from beneficial bacteria may be absorbed into specific cells of respective organs to suppress the outbreak of disease by regulating core immune functions and metabolic dysfunction.

*Lactobacillus paracasei* is a Gram-positive bacillus, and grows well not only in anaerobic environments but also in aerobic environments and is known as a beneficial bacterium that coexists in our bodies. Bacteria secrete extracellular vesicles (EVs) having a bilayer structure into the extracellular environment for the exchange of intercellular proteins, lipids, genes, and the like. Vesicles derived from gram-positive bacteria, such as *Lactobacillus paracasei*, include peptidoglycan and lipoteichoic acid, which are constituents of bacterial cell walls, in addition to bacteria-derived proteins and nucleic acids. In particular, the vesicles are absorbed into the cell and migrate to the endoplasmic reticulum (ER), and a viral membrane is formed in the ER even during viral replication.

However, there has been no known case where vesicles secreted from *Lactobacillus paracasei* are used for preventing, treating, or alleviating viral infectious diseases or respiratory diseases caused by viruses, bacterial factors, and the like.

DISCLOSURE

Technical Problem

As a result of intensive studies to solve the aforementioned problems, the present inventors confirmed that when vesicles were isolated from *Lactobacillus paracasei* bacteria and orally administered, the vesicles were delivered to the lungs, and when the vesicles were orally administered to a respiratory disease animal model caused by chemical, viral, and bacterial causative factors, and the like, the occurrence of the respiratory disease was significantly suppressed. Further, the present inventors confirmed that when vesicles derived from *Lactobacillus paracasei* were orally administered to a COVID-19 virus-infected hamster model, the replication of the COVID-19 virus was remarkably suppressed and the occurrence of pneumonia was significantly suppressed at the same time. In addition, the present inventors confirmed that when vesicles derived from *Lactobacillus paracasei* were orally administered to an influenza virus-infected mouse model, clinical symptoms caused by the influenza virus were significantly suppressed, thereby completing the present invention based on this.

Thus, the present invention is directed to providing a pharmaceutical composition for preventing or treating a viral infectious disease or a respiratory disease, comprising vesicles derived from *Lactobacillus paracasei* as an active ingredient.

In addition, the present invention is directed to providing a food composition for preventing or alleviating a viral infectious disease or a respiratory disease, comprising vesicles derived from *Lactobacillus paracasei* as an active ingredient.

In addition, the present invention is directed to providing an inhalant composition for preventing or treating a viral infectious disease or a respiratory disease, comprising vesicles derived from *Lactobacillus paracasei* as an active ingredient.

In addition, the present invention is directed to providing a cosmetic composition for preventing or alleviating a viral infectious disease, comprising vesicles derived from *Lactobacillus paracasei* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a pharmaceutical composition for preventing or treating a viral infectious disease or a respiratory disease, comprising vesicles derived from *Lactobacillus paracasei* as an active ingredient.

In addition, the present invention provides a food composition for preventing or alleviating a viral infectious disease or a respiratory disease, comprising vesicles derived from *Lactobacillus paracasei* as an active ingredient.

In addition, the present invention provides an inhalant composition for preventing or treating a viral infectious disease or a respiratory disease, comprising vesicles derived from *Lactobacillus paracasei* as an active ingredient.

In addition, the present invention provides a cosmetic composition for preventing or alleviating a viral infectious disease, comprising vesicles derived from *Lactobacillus paracasei* as an active ingredient.

As an exemplary embodiment of the present invention, the viral infectious disease may be any one or more viral infectious diseases selected from the group consisting of coronavirus, picornavirus, alphavirus, influenza virus, rhabdovirus, retrovirus, hepatitis B virus, hepatitis A virus, hepatitis C virus, adenovirus, herpes virus, poxvirus, parvovirus, reovirus, respiratory syncytial virus (RSV), and parainfluenza virus infectious disease, but is not limited thereto.

As another exemplary embodiment of the present invention, the coronavirus infectious disease may be any one or more selected from the group consisting of the common cold, severe acute respiratory syndrome (SARS), Middle East respiratory syndrome (MERS), and coronavirus infection disease-19 (COVID-19), but is not limited thereto.

As still another exemplary embodiment of the present invention, the picornavirus infectious disease may be any one or more selected from the group consisting of a rhinovirus infectious disease and an enterovirus infectious disease, but is not limited thereto.

As yet another exemplary embodiment of the present invention, the alphavirus infectious disease may be any one or more viral infectious diseases selected from the group consisting of Barmah Forest virus, chikungunya virus, Eastern equine encephalitis virus, Mayaro virus, o'nyong'nyong virus, Ross River virus, Semliki Forest virus, Sindbis virus, Tonate virus, Una virus, Venezuelan equine encephalitis virus, and Western equine encephalitis virus infectious disease, but is not limited thereto.

As yet another exemplary embodiment of the present invention, the retrovirus infectious disease may be any one or more viral infectious diseases selected from the group consisting of Avian leukosis virus, Rous sarcoma virus, Mouse mammary tumour virus, Murine leukemia virus, Feline leukemia virus, Bovine leukemia virus, Human T-lymphtrophic virus, and Human immunodeficiency virus (HIV) infectious disease, but is not limited thereto.

As yet another exemplary embodiment of the present invention, the herpes virus infectious disease may be any one or more viral infectious diseases selected from the group consisting of Herpes simplex virus-1 (HSV-1), Herpes simplex virus-2 (HSV-2), Varicella zoster virus (VSZ), Epstein-Barr virus (EBV), Cytomegalovirus (CMV), Roseolovirus, and Kaposi's sarcoma-associated herpesvirus (KSHV) infectious disease, but is not limited thereto.

As yet another exemplary embodiment of the present invention, the respiratory disease may be one or more diseases selected from the group consisting of acute rhinitis, chronic rhinitis, acute sinusitis, chronic sinusitis, dysosmia, acute bronchitis, chronic bronchitis, acute bronchiolitis, chronic bronchiolitis, viral pneumonia, bacterial pneumonia, interstitial pneumonitis, vascular pneumonia, and idiopathic pulmonary fibrosis, but is not limited thereto.

As yet another exemplary embodiment of the present invention, the vesicles may have an average diameter of 10 nm to 300 nm, but are not limited thereto.

As yet another exemplary embodiment of the present invention, the vesicles may be isolated from a culture solution of *Lactobacillus paracasei*, but are not limited thereto.

As yet another exemplary embodiment of the present invention, the vesicles may be obtained using vesicles isolated from food prepared by adding *Lactobacillus paracasei*, but are not limited thereto.

As yet another exemplary embodiment of the present invention, the vesicles may be naturally secreted from *Lactobacillus paracasei* or artificially produced, but are not limited thereto.

In addition, the present invention provides a method for preventing, treating, or alleviating a viral infectious disease or a respiratory disease, the method comprising administering the composition comprising vesicles derived from *Lactobacillus paracasei* as an active ingredient to a subject.

In addition, the present invention provides a use of vesicles derived from *Lactobacillus paracasei* for preventing, treating, or alleviating a viral infectious disease or a respiratory disease.

In addition, the present invention provides a use of vesicles derived from *Lactobacillus paracasei* for preparing a drug for treating a viral infectious disease or a respiratory disease.

Advantageous Effects

The present inventors confirmed that when vesicles were isolated from *Lactobacillus paracasei* bacteria and orally administered, the vesicles were delivered to the lungs, and when the vesicles were orally administered to a respiratory disease animal model caused by chemical, viral, and bacterial causative factors, and the like, the occurrence of the respiratory disease was significantly suppressed. Further, the present inventors confirmed that when vesicles derived from *Lactobacillus paracasei* were orally administered to a COVID-19-infected hamster model, the replication of the COVID-19 virus was remarkably suppressed and the occurrence of pneumonia was significantly suppressed at the same time. In addition, the present inventors confirmed that when vesicles derived from *Lactobacillus paracasei* were orally administered to an influenza virus-infected mouse model, clinical symptoms caused by the influenza virus were significantly suppressed. Thus, the vesicles derived from *Lactobacillus paracasei* according to the present invention are expected to be able to be usefully used as a composition for preventing, alleviating, or treating a viral infectious disease or a respiratory disease.

MODES OF THE INVENTION

Figure 1A:
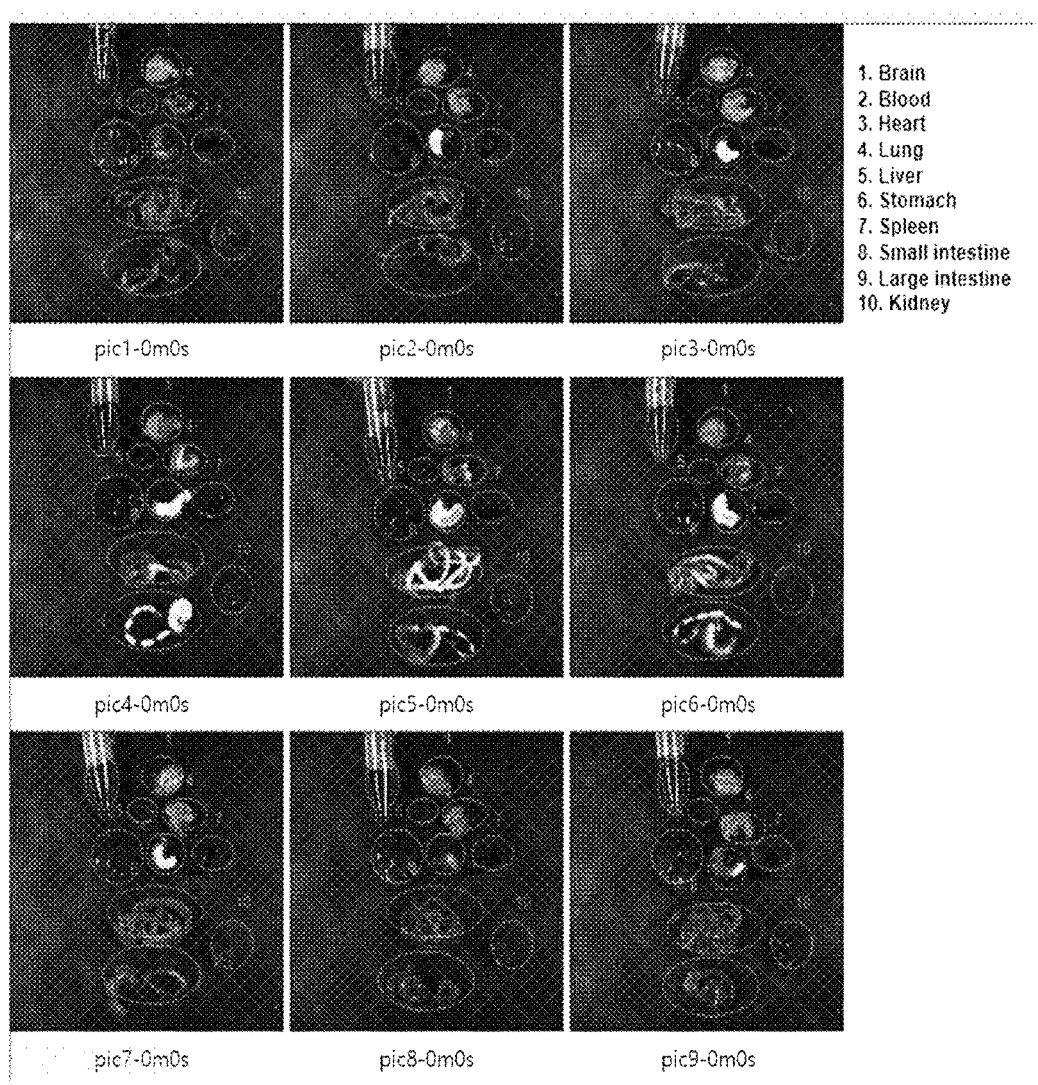
FIG. 1A is a set of photographs of the distribution of vesicles derived from *Lactobacillus paracasei* taken over time after orally administering the vesicles to mice.

In the present invention, it was confirmed that vesicles derived from *Lactobacillus paracasei* exhibited a remarkable treatment effect in a viral infectious disease or a respiratory disease by not only effectively suppressing the replication of virus during viral infection, but also effectively suppressing the occurrence of a respiratory disease caused by viral, bacterial, and chemical factors. Therefore, the vesicles derived from *Lactobacillus paracasei* of the present invention are expected to be able to be usefully used as a use of preventing, treating, or alleviating various viral infectious diseases or respiratory diseases.

In an example of the present invention, as a result of isolating vesicles from *Lactobacillus paracasei* bacteria (see Example 1) and confirming pharmacokinetic properties when the vesicles derived from *Lactobacillus paracasei* were orally administered, it was observed that the vesicles derived from *Lactobacillus paracasei* gradually spread in the body as time passed, and it was confirmed that fluorescent signals were maintained up to 48 hours after the vesicles were orally administered to the lungs (see Example 2).

In another example of the present invention, as a result of inducing viral pneumonia in mice and orally administering vesicles derived from *Lactobacillus paracasei*, it was confirmed that the number of total cells, the number of macrophages, and the number of neutrophils in a bronchoalveolar lavage fluid, which are indices from which the degree of pulmonary inflammation can be known, were remarkably decreased in a group to which the vesicles derived from *Lactobacillus paracasei* were administered compared to a positive control (Poly(I:C)), that the expression levels of TNF-α and IL-6, which are inflammatory cytokines, in the bronchoalveolar lavage fluid, were also decreased compared to the positive control, and that the infiltration of inflammatory cells into lung tissue was also decreased compared to the positive control. Through this, it could be seen that the vesicles derived from *Lactobacillus paracasei* efficiently suppressed the occurrence of pneumonia caused by viral causative factors (see Example 3).

In still another example of the present invention, as a result of inducing COVID-19 viral infection in hamsters and orally administering vesicles derived from *Lactobacillus paracasei*, the body weights were continuously decreased in a positive control (G2), but a decrease in body weight was remarkably decreased in groups to which vesicles derived from *Lactobacillus paracasei* were administered (G3, G4), and as a result of removing lung tissue and performing H&E staining, it was confirmed that the severity of pneumonia caused by COVID-19 viral infection was reduced by the vesicles derived from *Lactobacillus paracasei* and the degree of infiltration of inflammatory cells in the lung interstitium and around blood vessels was suppressed in a dose-dependent manner in the lung tissue. Further, it was confirmed that a gene for an envelope protein in lung tissue was remarkably decreased in the groups to which vesicles derived from *Lactobacillus paracasei* compared to the positive control, so it could be seen that the vesicles derived from *Lactobacillus paracasei* not only suppressed pneumonia caused by the COVID-19 virus in a dose-dependent manner, but also significantly suppressed the replication of the COVID-19 virus (see Example 4).

In yet another example of the present invention, as a result of inducing influenza virus infection in mice and orally administering vesicles derived from *Lactobacillus paracasei*, it was confirmed that the survival rates of groups to which the vesicles derived from *Lactobacillus paracasei* were administered (G3, G4) were increased and the decreased body weights were restored compared to the positive control (G2). In addition, it was confirmed that the decreased body temperature of the groups to which the vesicles derived from *Lactobacillus paracasei* were administered was restored and that a clinical symptom score was significantly improved, so it could be seen that the vesicles derived from *Lactobacillus paracasei* alleviated clinical symptoms caused by influenza virus infection in a dose-dependent manner (see Example 5).

In yet another example of the present invention, as a result of inducing bacterial pneumonia in mice and orally administering vesicles derived from *Lactobacillus paracasei*, it was confirmed that the number of total cells, the number of macrophages, and the number of neutrophils in a bronchoalveolar lavage fluid, which are indices from which the degree of pulmonary inflammation can be known, were remarkably decreased in a group to which the vesicles derived from *Lactobacillus paracasei* were administered compared to a positive control (EcEV), and that in addition to the expression levels of TNF-α, which is an inflammatory cytokine, MPO, which is a neutrophil activation marker, and NE in the bronchoalveolar lavage fluid, the infiltration of inflammatory cells into lung tissue was also decreased in the group to which the vesicles derived from *Lactobacillus paracasei* were administered. Through this, it could be seen that the vesicles derived from *Lactobacillus paracasei* efficiently suppressed the occurrence of pneumonia caused by bacterial causative factors (see Example 6).

In another experimental example of the present invention, as a result of inducing idiopathic pulmonary fibrosis caused by Bleomycin in mice and orally administering vesicles derived from *Lactobacillus paracasei*, it was confirmed that the number of neutrophils in a bronchoalveolar lavage fluid, which is an index from which the degree of pulmonary inflammation can be known, was decreased in a dose-dependent manner in a group to which the vesicles derived from *Lactobacillus paracasei* were administered compared to a positive control (BLM) and that the expression levels of α-SMA and p-smad3, which are important indices in the fibrosis process, were reduced in the group to which the vesicles derived from *Lactobacillus paracasei*. Furthermore, as a result of observing lung histological changes by H&E and Masson's trichrome staining, it was confirmed that the infiltration of inflammatory cells and the deposition of collagen fibers were reduced in the group to which the vesicles derived from *Lactobacillus paracasei* were administered compared to the positive control. Through this, it could be seen that the vesicles derived from *Lactobacillus paracasei* effectively suppressed the occurrence of idiopathic pulmonary fibrosis caused by Bleomycin, which is a chemical causative factor (see Example 7).

Thus, the present invention provides a pharmaceutical composition for preventing or treating a viral infectious disease or a respiratory disease, comprising vesicles derived from *Lactobacillus paracasei* as an active ingredient.

As used herein, the "viral infectious disease" refers to an infectious disease caused by introduction of a virus into the body, and the "infection" refers to a state in which a pathogenic microorganism invades the body of a host organism and grows and proliferates.

In the present invention, the viral infectious disease may be an infectious disease caused by viruses comprising, for example, coronavirus, picornavirus, alphavirus, influenza virus, rhabdovirus, retrovirus, hepatitis B virus, hepatitis A virus, hepatitis C virus, adenovirus, herpes virus, poxvirus, parvovirus, reovirus, respiratory syncytial virus (RSV), parainfluenza virus, and the like, but is not limited thereto.

As used herein, the "coronavirus" refers to a single-stranded positive RNA virus with an envelope, has a genome size of 25 to 32 kb, and is a relatively large virus among RNA viruses known to date. It is said to have a specific structure in the shape of a flame or crown because of the spike protein, which is a club-shaped protrusion, embedded in the envelope, and the virus name is said to be derived from the Latin word Corona. It is known that after being first discovered in chickens in 1937, coronaviruses have been found in various birds and animals such as bats, birds, cats, dogs, cows, pigs, and mice, and may cause various diseases such as gastrointestinal and respiratory diseases in animals.

In the present invention, the coronavirus infectious disease may be any one or more selected from the group consisting of the common cold, severe acute respiratory syndrome (SARS), Middle East respiratory syndrome (MERS), and coronavirus infection disease-19 (COVID-19), but is not limited thereto.

In the present invention, the picornavirus infectious disease may be any one or more selected from the group consisting of a rhinovirus infectious disease and an enterovirus infectious disease, but is not limited thereto.

In the present invention, the alphavirus infectious disease may be any one or more viral infectious diseases selected from the group consisting of Barmah Forest virus, chikungunya virus, Eastern equine encephalitis virus, Mayaro virus, o'nyong'nyong virus, Ross River virus, Semliki Forest virus, Sindbis virus, Tonate virus, Una virus, Venezuelan equine encephalitis virus, and Western equine encephalitis virus infectious disease, but is not limited thereto.

In the present invention, the retrovirus infectious disease may be any one or more viral infectious diseases selected from the group consisting of Avian leukosis virus, Rous sarcoma virus, Mouse mammary tumour virus, Murine leukemia virus, Feline leukemia virus, Bovine leukemia virus, Human T-lymphtrophic virus, and Human immunodeficiency virus (HIV) infectious disease, but is not limited thereto.

In the present invention, the herpes virus infectious disease may be any one or more viral infectious diseases selected from the group consisting of Herpes simplex virus-1 (HSV-1), Herpes simplex virus-2 (HSV-2), Varicella zoster virus (VSZ), Epstein-Barr virus (EBV), Cytomegalovirus (CMV), Roseolovirus, and Kaposi's sarcoma-associated herpesvirus (KSHV) infectious disease, but is not limited thereto.

As used herein, the "influenza virus" refers to a single-stranded RNA virus belonging to the family Orthomyxoviridae. When a person is infected with the influenza virus, influenza (flu) is induced, and the flu affects the upper respiratory system (nose, neck) or the lower respiratory system (lungs), and is accompanied by general physical symptoms such as sudden high fever, a headache, muscle pain, and general weakness.

As used herein, the "respiratory disease" refers to a disease of the respiratory system, which is induced by chemical, viral, or bacterial causative factors, and may include, for example, acute rhinitis, chronic rhinitis, acute sinusitis, chronic sinusitis, dysosmia, acute bronchitis, chronic bronchitis, acute bronchiolitis, chronic bronchiolitis, viral pneumonia, bacterial pneumonia, interstitial pneumonitis, vascular pneumonia, idiopathic pulmonary fibrosis, and the like, but is not limited thereto.

As used herein, the "pneumonia" refers to inflammation of the lungs caused by infection with microorganisms such as bacteria or viruses, and molds. Pulmonary symptoms that impair the normal function of the lungs, such as coughing, phlegm due to excretion of inflammatory materials, and dyspnea due to impaired respiratory function, gastrointestinal symptoms such as nausea, emesis, and diarrhea, and systemic diseases over the entire body, such as headache, fatigue, muscle pain and arthralgia may occur.

As used herein, the term "extracellular vesicle" or "vesicle" refers to a structure formed of a nano-sized membrane secreted from various bacteria, and in the present invention, the term collectively refers to all structures formed of a membrane naturally secreted from Lactobacillus paracasei, or artificially produced. The vesicles may be isolated from a culture solution including bacterial cells of Lactobacillus paracasei by using one or more methods selected from the group consisting of heating, centrifugation, ultra-high speed centrifugation, high pressure treatment, extrusion, sonication, cell lysis, homogenization, freezing-thawing, electroporation, mechanical decomposition, chemical treatment, filtration by filter, gel filtration chromatography, free-flow electrophoresis, and capillary electrophoresis. Further, a process such as washing for removing impurities and concentration of obtained vesicles may be further included.

In the present invention, the vesicles may be vesicles isolated from a culture solution of Lactobacillus paracasei, or from a food product prepared by adding Lactobacillus paracasei, but is not limited thereto.

In the present invention, the vesicles derived from Lactobacillus paracasei may have an average diameter 10 nm to 1000 nm, 10 nm to 900 nm, 10 nm to 800 nm, 10 nm to 700 nm, 10 nm to 600 nm, 10 nm to 500 nm, 10 nm to 400 nm, 10 nm to 300 nm, or 10 nm to 200 nm, but the average diameter is not limited thereto.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC), HPMC 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC), HPMC 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan(propylene glycol monostearate), glycerin, Adeps solidus, buytyrum Tego-G, cebes Pharma 16, hexalide base 95, cotomar, Hydrokote SP, S-70-XXA, S-70-XX75(S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to a subject via various routes. All administration methods can be predicted, and the pharmaceutical composition may be administered via, for example, oral administration, subcutaneous injection, intraperitoneal injection, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases.

As another aspect of the present invention, the present invention provides a food composition for preventing or alleviating a viral infectious disease or a respiratory disease, comprising vesicles derived from *Lactobacillus paracasei* as an active ingredient.

In the present invention, the food composition may be a health functional food composition, but is not limited thereto.

The vesicles derived from *Lactobacillus paracasei* according to the present invention may be used by adding the vesicles derived from *Lactobacillus paracasei* as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

As another aspect of the present invention, the present invention provides an inhalant composition for preventing or treating a viral infectious disease or a respiratory disease, comprising vesicles derived from *Lactobacillus paracasei* as an active ingredient.

In the inhalant composition of the present invention, the active ingredient may be added as it is to the inhalant, or may be used together with other ingredients, and may be appropriately used by a typical method. The mixing amount of the active ingredient may be suitably determined depending on the purpose of use (for prevention or treatment).

Examples of an inhalant for parenteral administration include an aerosol, a powder for inhalation or a liquid for inhalation, and the liquid for inhalation may be used by being dissolved or suspended in water or another suitable medium during use. These inhalants are prepared according to known methods. For example, the liquid for inhalation is formulated by appropriately selecting a preservative (benzalkonium chloride, paraben, and the like), a colorant, a buffering agent (sodium phosphate, sodium acetate, and the like), an isotonic agent (sodium chloride, concentrated glycerin, and the like), a thickener (carboxyvinyl polymer, and the like), an absorption enhancer, and the like, if necessary.

The powder for inhalation is formulated by appropriately selecting a lubricant (stearic acid and salts thereof, and the like), a binder (starch, dextrin, and the like), an excipient (lactose, cellulose, and the like), a colorant, a preservative (benzalkonium chloride, paraben, and the like), an absorption enhancer, and the like, if necessary.

The inhalant composition may be administered by an inhalant device, the inhalant device is a device capable of a composition to a subject, such as lung tissue of the subject, and examples thereof include an inhaler, a nebulizer or a ventilator. When a liquid for inhalation is administered, a nebulizer (atomizer, nebulizer) is typically used, and when a powder for inhalation is administered, an inhalation dispenser for powdered medicine is typically used.

As another aspect of the present invention, the present invention provides a cosmetic composition for preventing or alleviating a viral infectious disease, comprising vesicles derived from *Lactobacillus paracasei* as an active ingredient.

In the present invention, a cosmetic composition may contain the vesicles derived from *Lactobacillus paracasei* in an amount of 0.0005 to 50 wt % based on the total weight of the composition. Further, the composition of the present invention may further contain one or more active ingredients exhibiting the same or similar function in the vesicles derived from *Lactobacillus paracasei*.

A cosmetic prepared by the cosmetic composition of the present invention may be prepared in the form of a general emulsion formulation and a general solubilized formulation. Examples of a cosmetic of the emulsion formulation include nourishing lotion, cream, essence, and the like, and examples of a cosmetic of the solubilized formulation include softening lotion. In addition, by containing a dermatologically acceptable medium or base, the cosmetic may be prepared in the form of an auxiliary agent that may be topically or systemically applied and typically used in the dermatology field.

A suitable cosmetic formulation may be provided in the form of, for example, a solution, a gel, a solid or a kneaded anhydrous product, an emulsion obtained by dispersing an oil phase in an aqueous phase, a suspension, a microemulsion, a microcapsule, microgranules or an ionic (liposome) and non-ionic vesicular dispersing agent, a cream, a skin toner, a lotion, a powder, an ointment, a spray, or a conceal stick. Furthermore, the cosmetic composition may be prepared in the form of a foam or an aerosol composition that further contains a compressed propellant.

Further, the cosmetic composition of the present invention may additionally contain auxiliary agents typically used in the cosmetology or dermatology field, such as a fatty substance, an organic solvent, a solubilizing agent, a thickener and a gelling agent, a softener, an antioxidant, a suspending agent, a stabilizer, a foaming agent, an odorant, a surfactant, water, an ionic or a non-ionic emulsifier, a filler, a metal ion sequestering agent, a chelating agent, a preservative, a vitamin, a blocking agent, a wetting agent, an essential oil, a dye, a pigment, a hydrophilic or lipophilic active agent, a lipid vesicle, or any other ingredient typically used in cosmetics. In addition, the ingredients may be introduced in an amount generally used in the dermatology field.

Examples of a product to which the cosmetic composition of the present invention may be added include cosmetics such as astringent lotion, softening lotion, nourishing lotion, various creams, essences, packs, and foundations, a cleanser, a facial cleanser, soap, a treatment, a beauty liquid, and the like.

A specific formulation of the cosmetic composition of the present invention includes a formulation such as skin lotion, skin softener, skin toner, astringent, lotion, milk lotion, moisture lotion, nourishing lotion, massage cream, nourishing cream, moisture cream, hand cream, essence, nourishing essence, pack, soap, shampoo, cleansing foam, cleansing lotion, cleansing cream, body lotion, body cleanser, an emulsion, pressed powder, loose powder, and eye shadow.

As another aspect of the present invention, the present invention provides a method for preventing or treating a viral infectious disease or a respiratory disease, the method comprising administering a composition comprising vesicles derived from *Lactobacillus paracasei* as an active ingredient to a subject.

As another aspect of the present invention, the present invention provides a use of vesicles derived from *Lactobacillus paracasei* for preventing or treating a viral infectious disease or a respiratory disease.

As another aspect of the present invention, the present invention provides a use of vesicles derived from *Lactobacillus paracasei* for preparing a drug for treating a viral infectious disease or a respiratory disease.

As used herein, the term "prevention" as used herein means all actions that inhibit or delay the onset of a viral infectious disease or a respiratory disease. The term "treatment" as used herein means all actions that alleviate or beneficially change a viral infectious disease or a respiratory disease and abnormal metabolic symptoms caused thereby via administration of the pharmaceutical composition according to the present invention. The term "improvement" as used herein means all actions that reduce the degree of parameters related to a viral infectious disease or a respiratory disease, e.g., symptoms via administration of the composition according to the present invention.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

In the present invention, when one part "comprises" one constituent element, unless otherwise specifically described, this does not mean that another constituent element is excluded, but means that another constituent element may be further comprised.

Hereinafter, preferred Examples for helping the understanding of the present invention will be suggested. However, the following Examples are provided only to more easily understand the present invention, and the contents of the present invention are not limited by the following Examples.

EXAMPLES

Example 1

Isolation of Vesicles Derived from *Lactobacillus paracasei*

To isolate extracellular vesicles (EVs) derived from *Lactobacillus paracasei*, the *Lactobacillus paracasei* was inoculated into an MRS (de Man-Rogosa and Sharpe) medium, incubated at 37° C. and 200 rpm to have an absorbance ($OD_{600nm}$) of 1.0 to 1.5, and reinoculated into a Luria Bertani (LB) medium and incubated. Then, a supernatant from which bacterial cells had been removed was obtained by recovering the culture solution including bacterial cells and performing centrifugation at 4° C. and 10,000 g for 20 minutes. The obtained supernatant was again filtered using a 0.22 μm filter, and the filtered supernatant was concentrated to a volume of 50 mL or less using a 100 kDa Pellicon 2 Cassette filter membrane (Merck Millipore) and a MasterFlex pump system (Cole-Parmer). A vesicle derived from *Lactobacillus paracasei* was isolated by filtering the concentrated supernatant again using a 0.22 μm filter. The amount of protein included in the supernatant was measured using a Pierce BCA Protein Assay kit (Thermo Fisher Scientific). Vesicles (EcEV) derived from *Escheri-* chia coli, which is a bacterial causative factor, were also isolated by the same method as described above.

Example 2

Evaluation of Pharmacokinetic Characteristics of Vesicles Derived from Lactobacillus paracasei In order to investigate the pharmacokinetic characteristics of vesicles derived from Lactobacillus paracasei during oral administration, the fluorescence expressed in the body and each organ from immediately before administration to 72 hours after administration was measured by orally administering vesicles stained with a fluorescent staining reagent to mice.

Figure 1B:
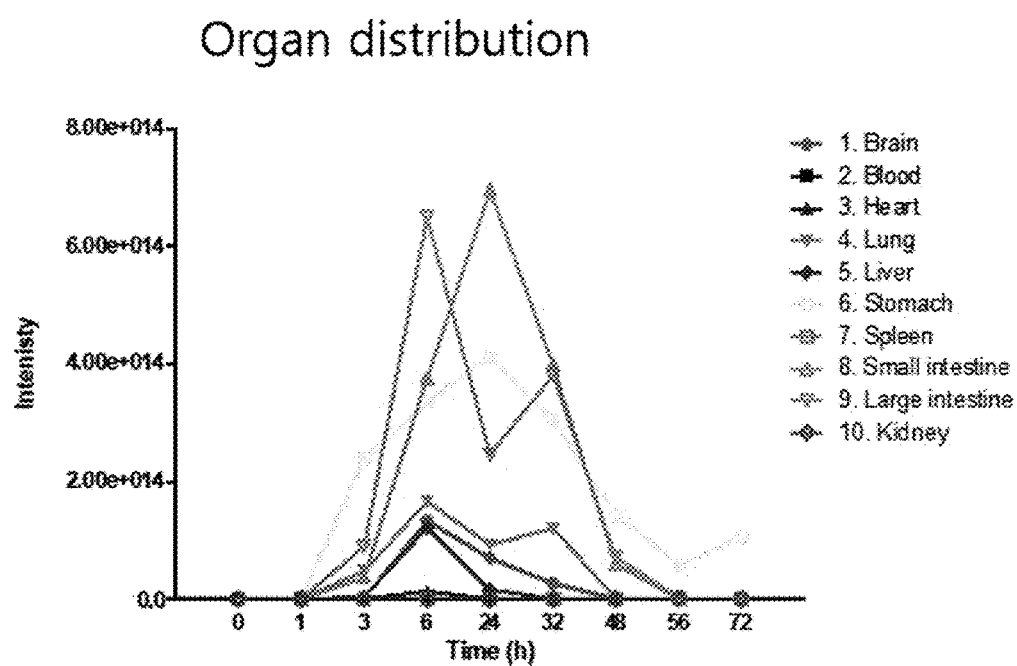
FIG. 1B shows a graph of the distribution of vesicles derived from *Lactobacillus paracasei* in each organ by orally administering the vesicles to mice and then removing various organs.

As a result, as illustrated in FIG. 1A, it was confirmed that the fluorescently stained Lactobacillus paracasei-derived vesicles gradually spread in the body over time. Further, as illustrated in FIG. 1B, when each organ was separately observed, a fluorescent signal of Lactobacillus paracasei-derived vesicles was observed in the stomach 1 hour after oral administration, and fluorescent signals were observed in the small intestine, large intestine, and lungs from 3 hours. In addition, it was confirmed that the fluorescent signals of the lungs were maintained for up to 48 hours.

Example 3

Figure 2:
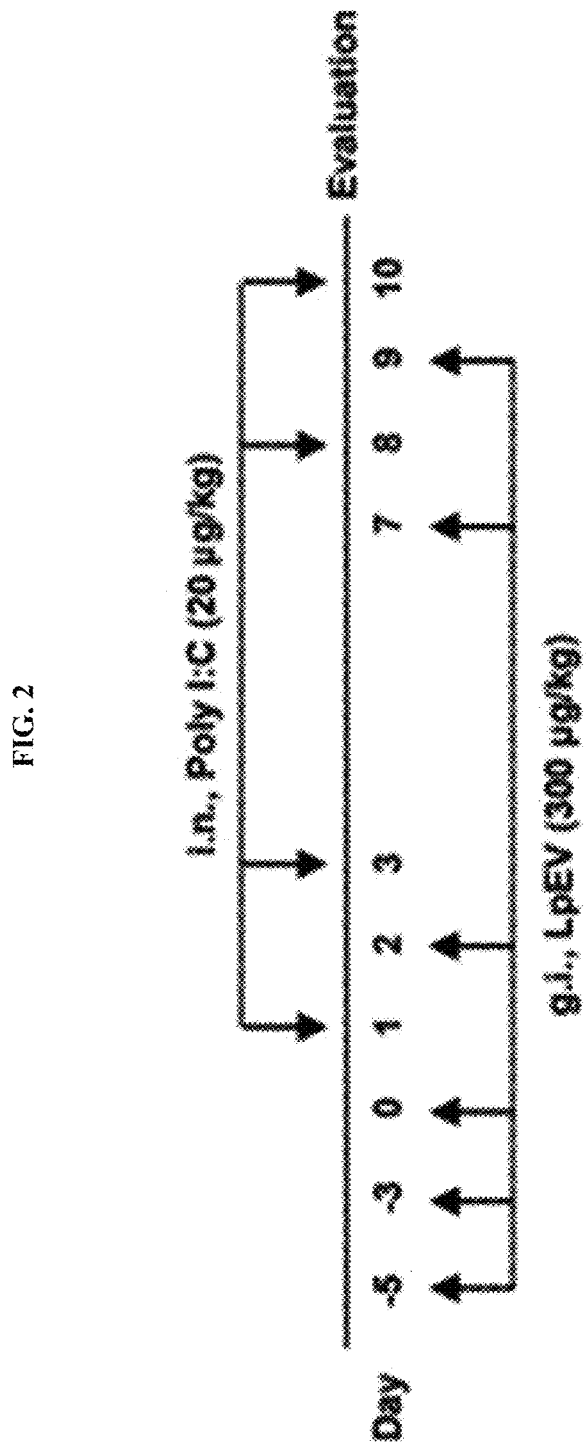
FIG. 2 illustrates an experimental method for evaluating the treatment effect of vesicles derived from *Lactobacillus paracasei* in a viral pneumonia mouse model.

Treatment Effect of Vesicles Derived from Lactobacillus paracasei in Viral Pneumonia Mouse Model In order to evaluate the treatment efficacy of Lactobacillus paracasei vesicles in a viral pneumonia mouse model, an experiment was performed as follows by the method specified in FIG. 2.

That is, after five 6-week-old female C57BL/6 mice were placed in each cage without discrimination and given an acclimation time of 2 days, viral pneumonia was induced by intranasally administering polyinosinic-polycytidylic acid (Poly(I:C)) (20 µg/kg) on days 1, 3, 8, and 10 after the start of the experiment. Furthermore, Lactobacillus paracasei vesicles (300 µg/kg) were orally administered on days 5, 3, and 0 before the start of the experiment, and also on days 2, 7, and 9 after the start of the experiment, using a sonde (load for oral administration).

According to the above method, a bronchoalveolar lavage fluid was secured by dissecting the mice 24 hours after the final administration of Poly(I:C), and the composition and degree of infiltration of immune cells and expression levels of TNF-α and IL-6, which are inflammatory cytokines, in the bronchoalveolar lavage fluid were analyzed. The degree of pulmonary inflammation was analyzed by removing lung tissue, performing H&E staining, and observing the lung tissue.

Figure 3:
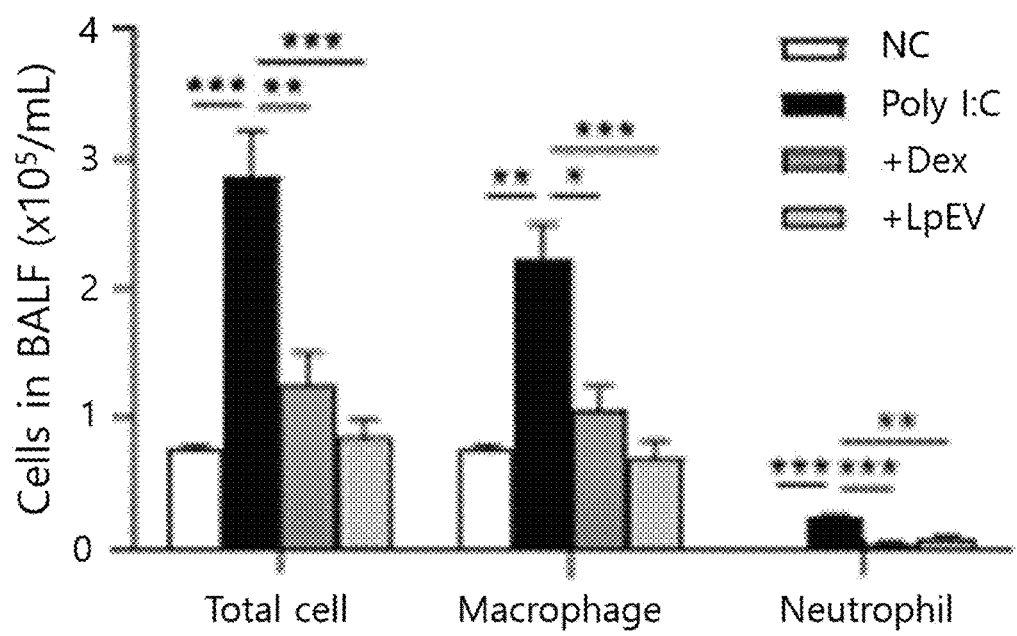
FIG. 3 illustrates the results of orally administering vesicles derived from *Lactobacillus paracasei* to a viral pneumonia mouse model and then evaluating the composition and number of inflammatory cells in a bronchoalveolar lavage fluid.

As a result, as illustrated in FIG. 3, it was confirmed that the number of total cells, the number of macrophages, and the number of neutrophils in a bronchoalveolar lavage fluid, which are indices from which the degree of pulmonary inflammation can be known, were remarkably decreased in a group to which the Lactobacillus paracasei vesicles were administered compared to a positive control (Poly(I:C)), showing an effect similar to that of a group to which a control drug dexamethasone was administered.

Figure 4:
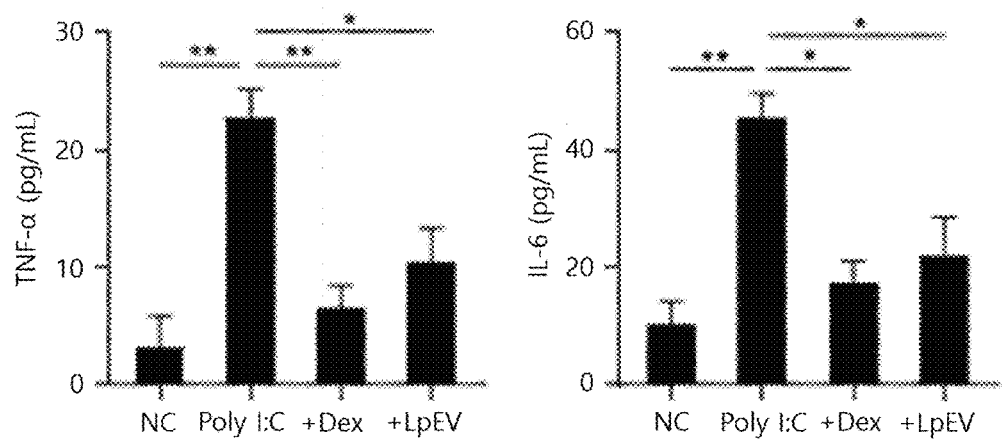
FIG. 4 illustrates the results of orally administering vesicles derived from *Lactobacillus paracasei* to a viral pneumonia mouse model and then quantifying TNF-α and IL-6, which are inflammatory cytokines, in a bronchoalveolar lavage fluid by an ELISA method.
Figure 5:
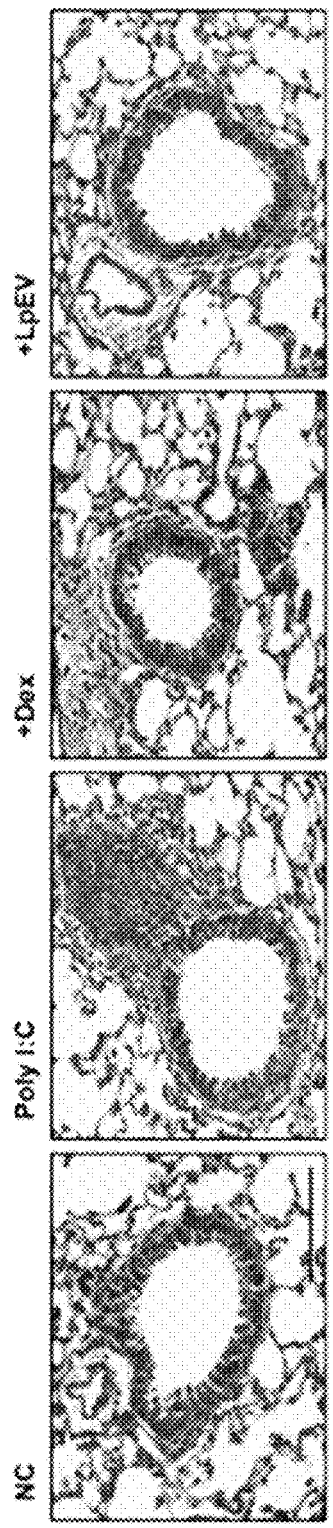
FIG. 5 illustrates the results of orally administering vesicles derived from *Lactobacillus paracasei* to a viral pneumonia mouse model and then evaluating the degree of infiltration of inflammatory cells by removing lung tissue and performing H&E staining on the lung tissue.

Further, as illustrated in FIG. 4, it was confirmed that the expression levels of TNF-α and IL-6, which are inflammatory cytokines, in a bronchoalveolar lavage fluid, were also decreased compared to the positive control, and as illustrated in FIG. 5, it was confirmed that the infiltration of inflammatory cells into lung tissue was also reduced in the group to which the Lactobacillus paracasei vesicles were administered compared to the positive control.

The results as described above mean that vesicles derived from Lactobacillus paracasei efficiently suppress the occurrence of pneumonia caused by viral causative factors.

Example 4

Figure 6:
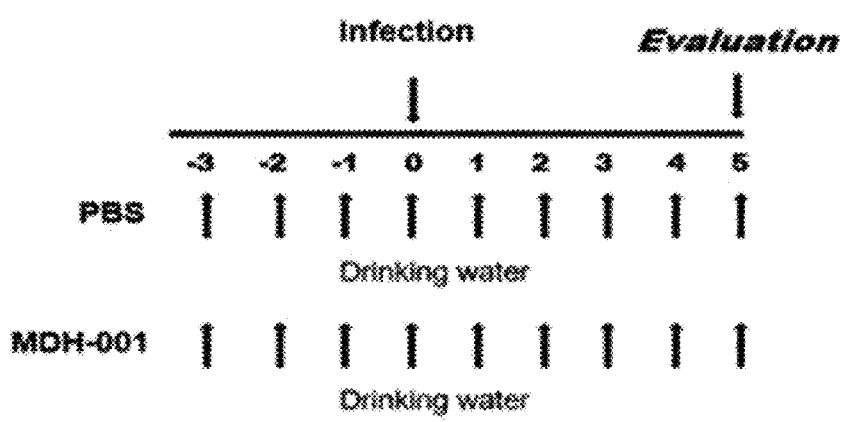
FIG. 6 illustrates an experimental method for evaluating the treatment effect of vesicles derived from *Lactobacillus paracasei* on viral infection in a COVID-19-infected hamster model.

Treatment Effect of Vesicles Derived from Lactobacillus paracasei in COVID-19-Infected Hamster Model In order to evaluate the treatment efficacy of vesicles derived from Lactobacillus paracasei in a COVID-19 virus-infected hamster model, an experiment was performed as follows by the method specified in FIG. 6.

That is, 8-week-old male Syrian hamsters (RjHan:AURA-strain hamsters) were distributed in a numbers of three to a negative control (G1), five to a positive control (G2), eight to a group to which a low dose of vesicles (MDH-001) derived from Lactobacillus paracasei was administered (2 mg/kg, G3), and eight to a group to which a high dose was administered (20 mg/kg, G4). In addition, vesicles derived from Lactobacillus paracasei were orally administered three times at 24-hour intervals from day 3 before viral infection. COVID-19 viral infection was performed by subculturing SARS-CoV-2 (NCCP43326), which is a publicly available virus and administering 200 µl of a $10^4$ $TCID_{50}$/mL virus solution to the left nasal cavity of the hamsters. Vesicles derived from Lactobacillus paracasei were orally administered at a low dose (2 mg/kg, G3) and a high dose (20 mg/kg, G4) five times at 24-hour intervals on the day of viral infection and until day 4 after infection. Body weights were measured during administration, lung tissue was removed by dissecting hamsters on day 5 after viral infection, and histological pathology was confirmed.

Figure 7:
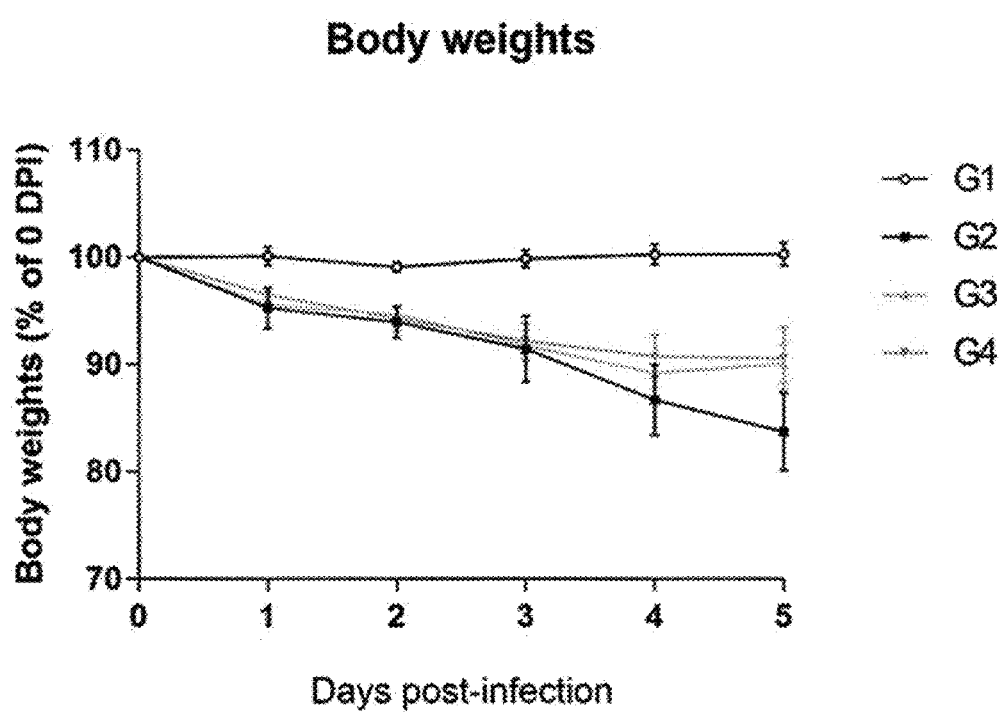
FIG. 7 illustrates the results of orally administering vesicles derived from *Lactobacillus paracasei* to a COVID-19-infected hamster model and then measuring the body weights of hamster individuals after inoculation of the COVID-19 virus.

As a result, as illustrated in FIG. 7, all body weights were decreased in the infected groups from day 1 after COVID-19 viral infection, body weights were continuously decreased in the positive control (G2) from day 3 after administration of the virus, but the decrease in body weight was remarkably reduced in the groups to which vesicles derived from Lactobacillus paracasei were administered (G3, G4).

Figure 8A:
FIG. 8A illustrates the results of orally administering vesicles derived from *Lactobacillus paracasei* to a COVID-19 virus-infected hamster model and then performing H&E staining by removing lung tissue.
Figure 8B:
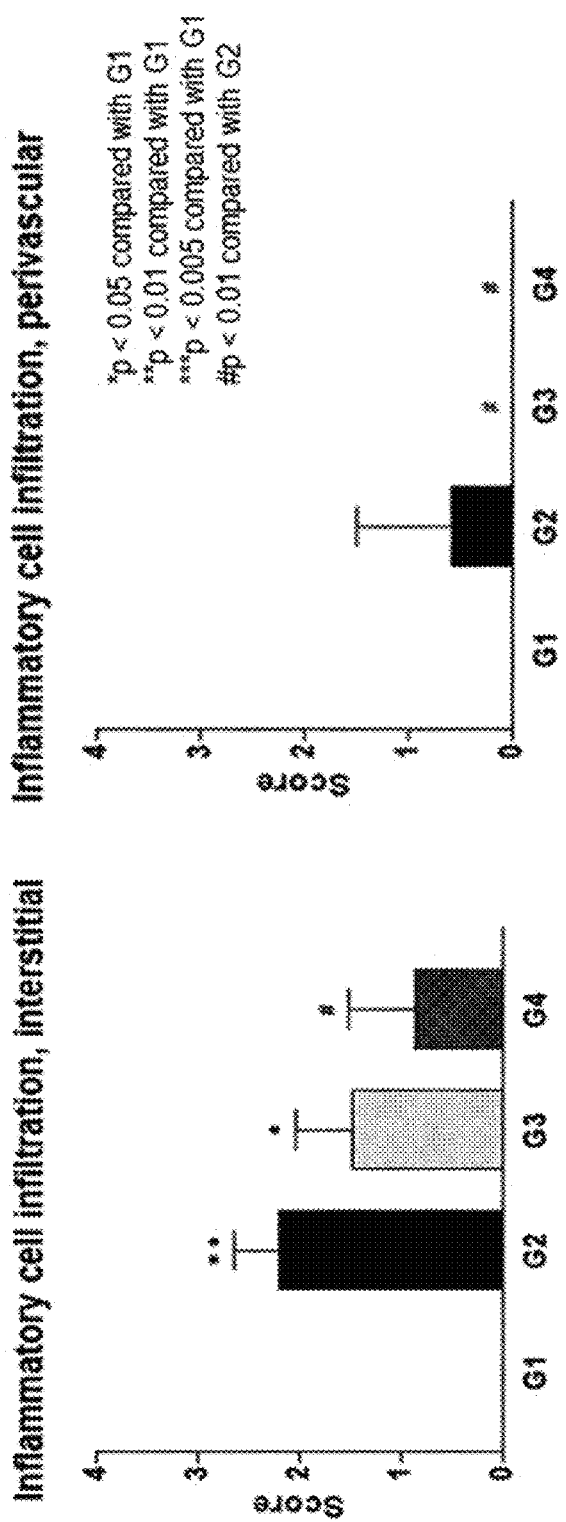
FIG. 8B illustrates the results of measuring the degree of infiltration of inflammatory cells in the lung interstitium and around blood vessels in lung tissue by observing lung tissue H&E staining slides.

Furthermore, lung tissue was removed on day 5 after COVID-19 viral infection, and the severity of pneumonia was evaluated by H&E staining (FIG. 8A), and the negative control (G1), the positive control (G2), the low dose of vesicles derived from Lactobacillus paracasei (G3), and the high dose of vesicles derived from Lactobacillus paracasei (G4) are shown sequentially from the left. As a result of H&E staining, as illustrated in FIG. 8A, it was confirmed that the severity of pneumonia caused by COVID-19 viral infection was reduced by vesicles derived from Lactobacillus paracasei. And then, the degree of infiltration of inflammatory cells in the lung interstitium and around blood vessels in lung tissue was measured by observing lung tissue H&E staining slides (FIG. 8B). As a result, as illustrated in FIGS. 8A and 8B, it was confirmed that the degree of interstitial pneumonia and the degree of vascular pneumonia caused by the COVID-19 virus were suppressed in a dose-dependent manner by vesicles derived from Lactobacillus paracasei.

Figure 9:
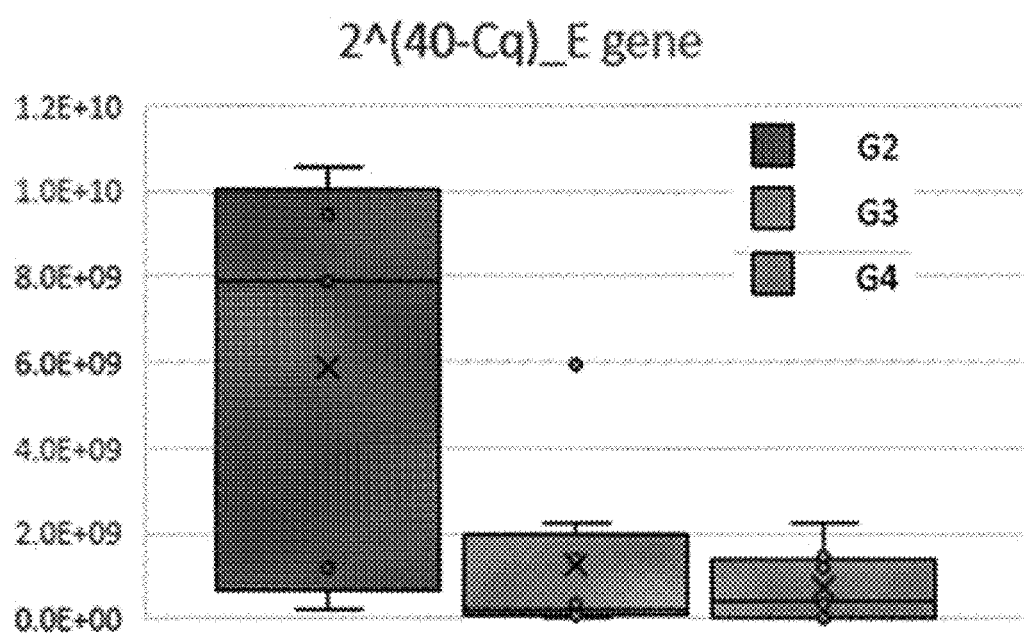
FIG. 9 illustrates the results of orally administering vesicles derived from *Lactobacillus paracasei* to a COVID-19 virus-infected hamster model and then quantifying the replication degree of the COVID-19 virus by a PCR method by targeting an envelope gene (E gene) of the virus in removed lung tissue.

In addition, lung tissue was removed on day 5 after COVID-19 viral infection, and the replication degree of COVID-19 virus was quantified by a real-time PCR method. As a result, as illustrated in FIG. 9, a gene for an envelope protein in the lung tissue was reduced to about 1/32 in the group to which vesicles derived from *Lactobacillus paracasei* were administered compared to the positive control.

The results as described above mean that vesicles derived from *Lactobacillus paracasei* not only suppress pneumonia caused by the COVID-19 virus in a dose-dependent manner, but also significantly suppress the replication of the COVID-19 virus.

Example 5

Figure 10:
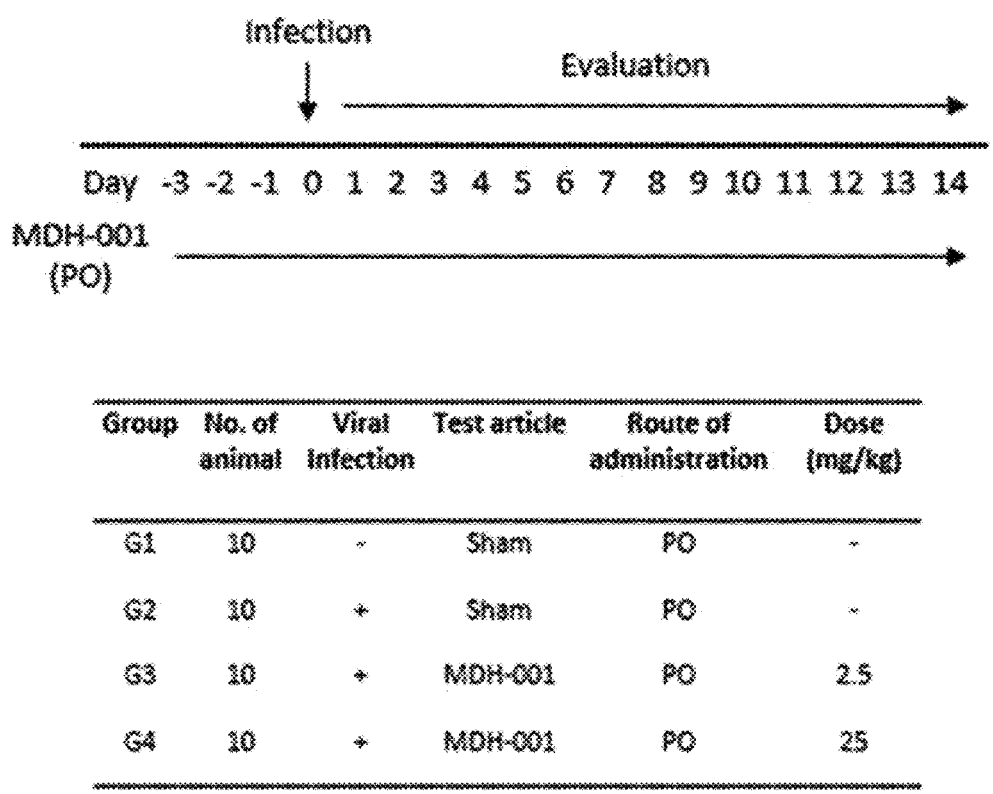
FIG. 10 illustrates an experimental method for evaluating the treatment effect of vesicles derived from *Lactobacillus paracasei* on viral infection in an influenza virus-infected mouse model.

Treatment Effect of Vesicles Derived from *Lactobacillus paracasei* in Influenza-Infected Mouse Model In order to evaluate the treatment efficacy of vesicles derived from *Lactobacillus paracasei* in an influenza virus-infected mouse model, an experiment was performed as follows by the method specified in FIG. 10.

That is, ten 8-week-old female C57BL/6 mice were assigned into each of a negative control, a positive control, a group to which a low dose of vesicles (MDH-001) derived from *Lactobacillus paracasei* was administered (2.5 mg/kg, G3), and a group to which a high dose of vesicles derived from *Lactobacillus paracasei* was administered (20 mg/kg, G4) without discrimination, and then the vesicles derived from *Lactobacillus paracasei* were orally administered three times at 24-hour intervals from three days before infection. For influenza viral infection, Influenza A virus (A/Puerto Rico/08/1934, H1N1) was inoculated into hatched fertilized eggs, the culture solution was recovered after 48 hours, and 30 μL of a viral solution of 1 $LD_{50}$, which was validated, was intranasally administered to the mice. 2.5 mg/kg (G3) and 25 mg/kg (G4) of vesicles derived from *Lactobacillus paracasei* were orally administered fourteen times at 24-hour intervals on the day of viral infection and for 13 days after the infection. During administration, general symptoms were observed, and body weights and body temperatures were measured. Survival rates were measured using 20% body weight loss as a criterion for euthanasia, and clinical symptoms were scored according to the behavior of mice.

Figure 11:
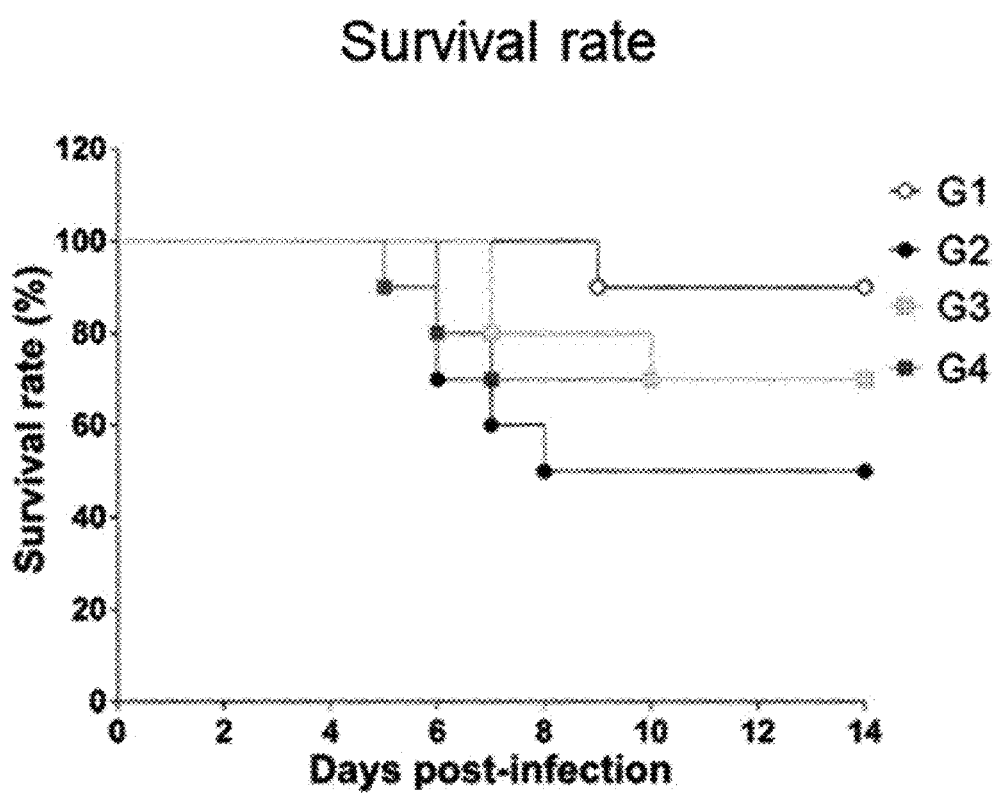
FIG. 11 illustrates the results of orally administering vesicles derived from *Lactobacillus paracasei* to an influenza virus-infected mouse model and then measuring the survival rate of mice after inoculation of the influenza virus.
Figure 12:
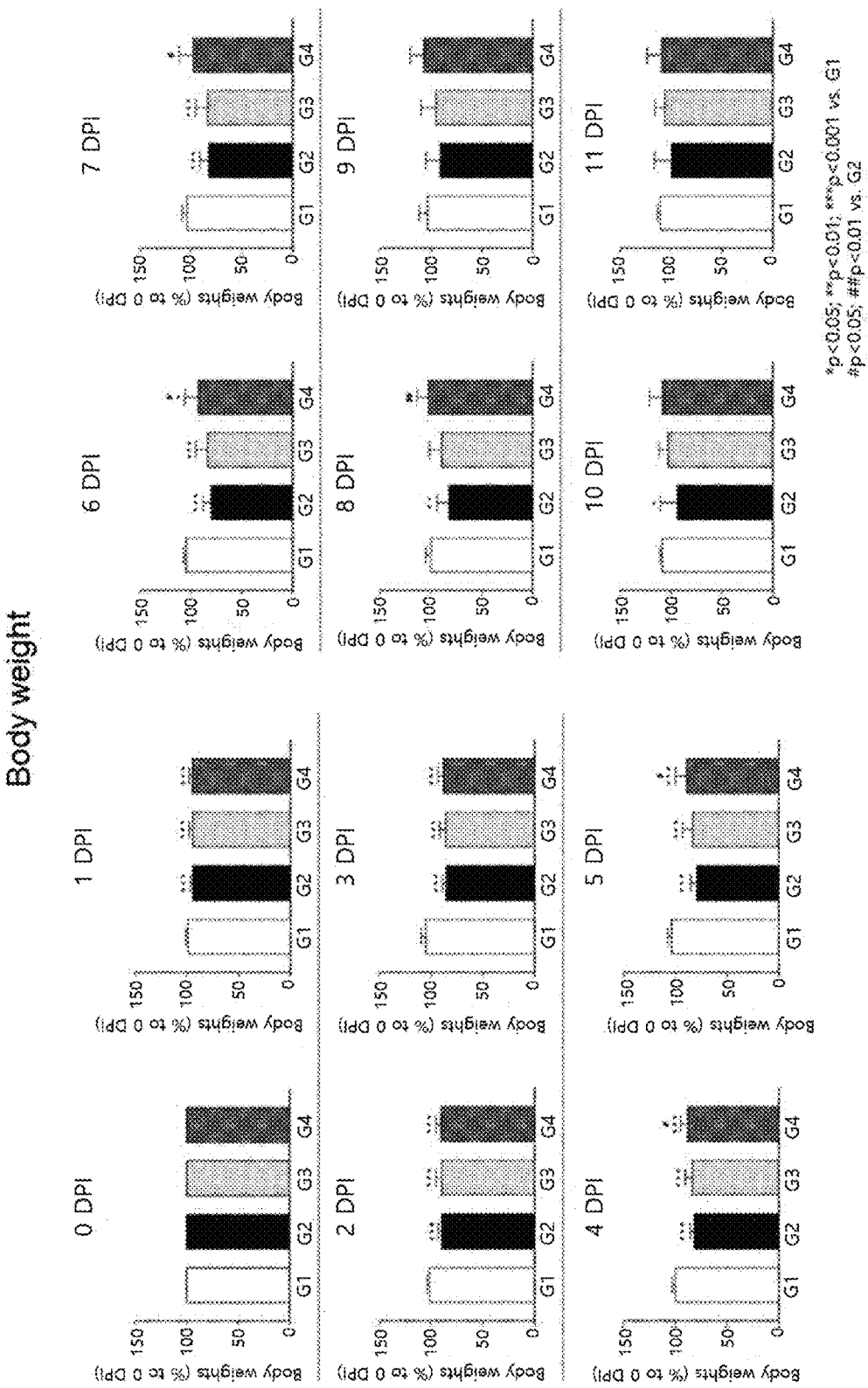
FIG. 12 illustrates the results of orally administering vesicles derived from *Lactobacillus paracasei* to an influenza virus-infected mouse model and then measuring the changes in body weights of mice after inoculation of the influenza virus.

As a result, as illustrated in FIG. 11, the survival rates of the groups to which vesicles derived from *Lactobacillus paracasei* (G3, G4) were increased compared to the positive control (G2). Furthermore, as illustrated in FIG. 12, body weights in all the groups infected with the influenza virus were reduced from day 1 after infection, and in the group to which a low dose of vesicles derived from *Lactobacillus paracasei* was administered, body weights began to be restored from day 6 after infection, and were increased to a level similar to those of the normal control on day 10 after infection.

In addition, in the group to which a high dose of vesicles derived from *Lactobacillus paracasei* was administered (G4), body weights began to be restored from day 4 after infection, and were increased to a level similar to those of the normal control on day 8 after infection.

Figure 13:
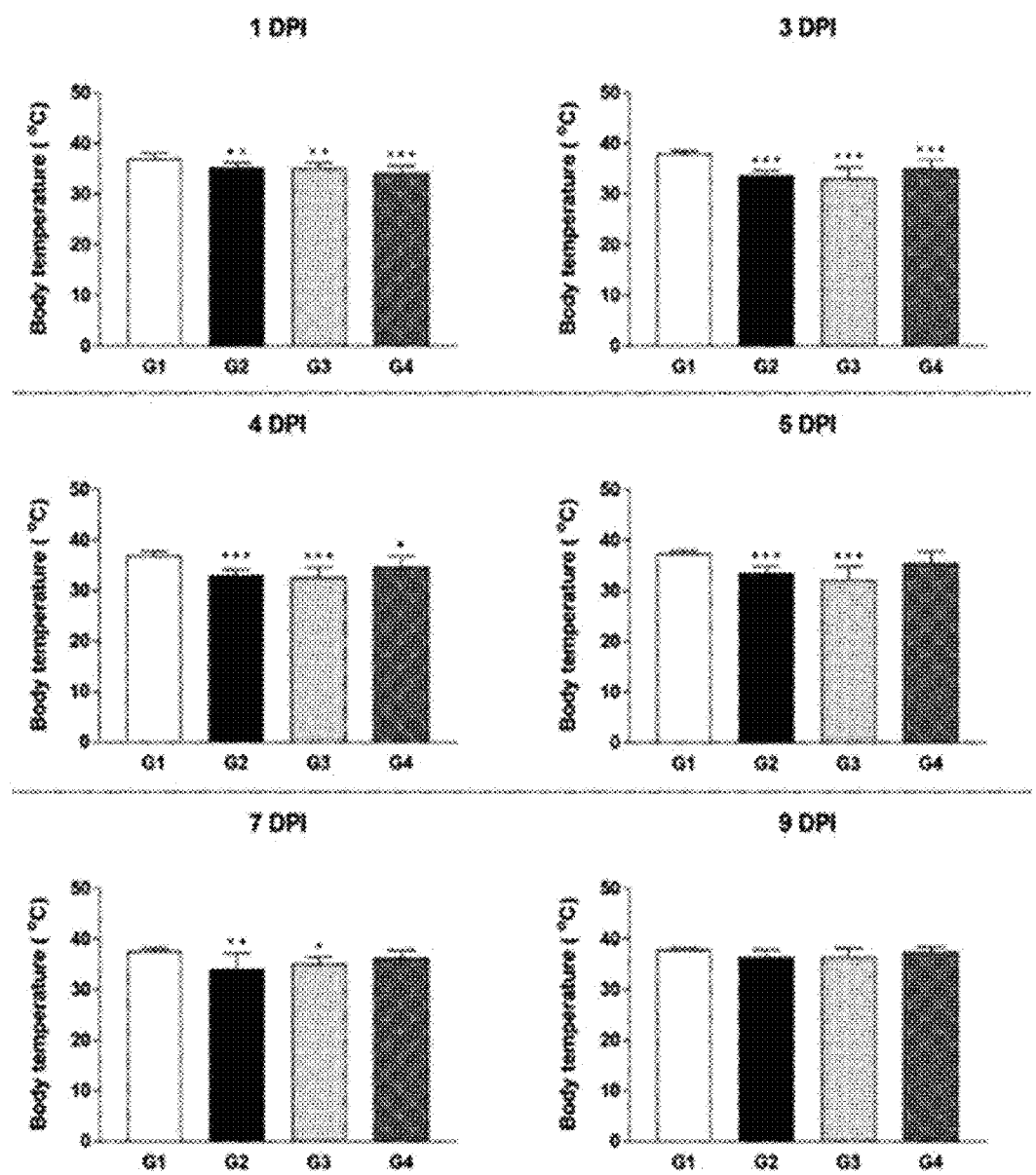
FIG. 13 illustrates the results of orally administering vesicles derived from *Lactobacillus paracasei* to an influenza virus-infected mouse model and then measuring the changes in body temperature of mice after inoculation of the influenza virus.

Furthermore, as illustrated in FIG. 13, the body temperature of the group to which a low dose of vesicles derived from *Lactobacillus paracasei* was administered (G3) was decreased up to day 5 after infection, again increased from day 7 after infection, and increased from day 9 to a level similar to that of the normal control. Further, the body temperature of the group to which a high dose of vesicles derived from *Lactobacillus paracasei* was administered (G4) showed a tendency to be restored from day 4 after infection, and was increased to a level similar to that of the normal control on day 5 after infection.

Figure 14:
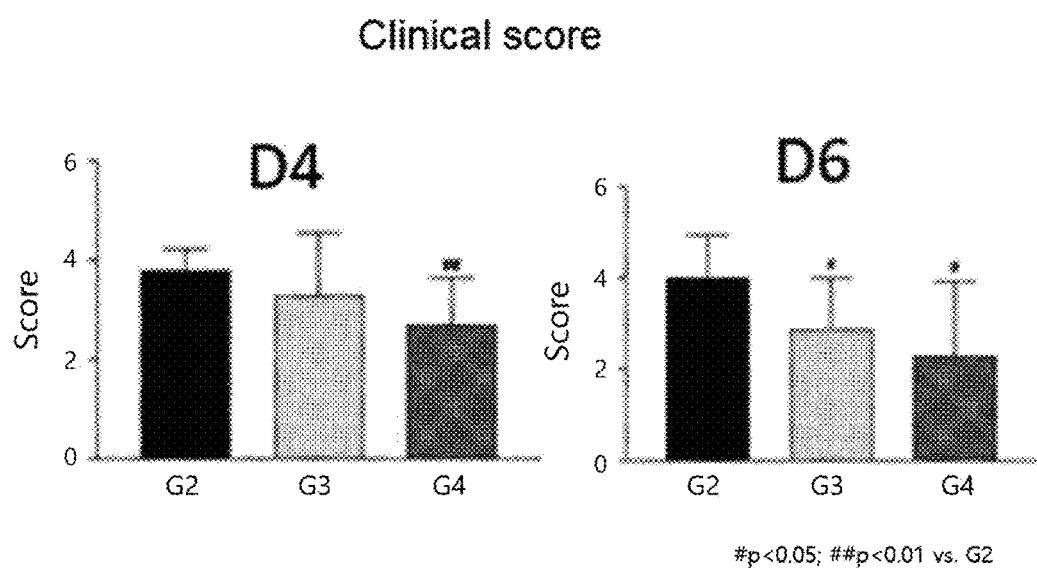
FIG. 14 illustrates the results of orally administering vesicles derived from *Lactobacillus paracasei* to an influenza virus-infected mouse model and then measuring the clinical symptoms of mice after inoculation of the influenza virus.

In addition, as illustrated in FIG. 14, the clinical symptom scores of the groups to which vesicles derived from *Lactobacillus paracasei* were administered were significantly decreased in the high-dose administration group on day 4 of infection, and clinical symptoms were significantly alleviated in both low-dose and high-dose administration groups on day 6 of infection.

Through the results described above, it could be seen that vesicles derived from *Lactobacillus paracasei* alleviate the clinical symptoms caused by influenza viral infection in a dose-dependent manner.

Example 6

Figure 15:
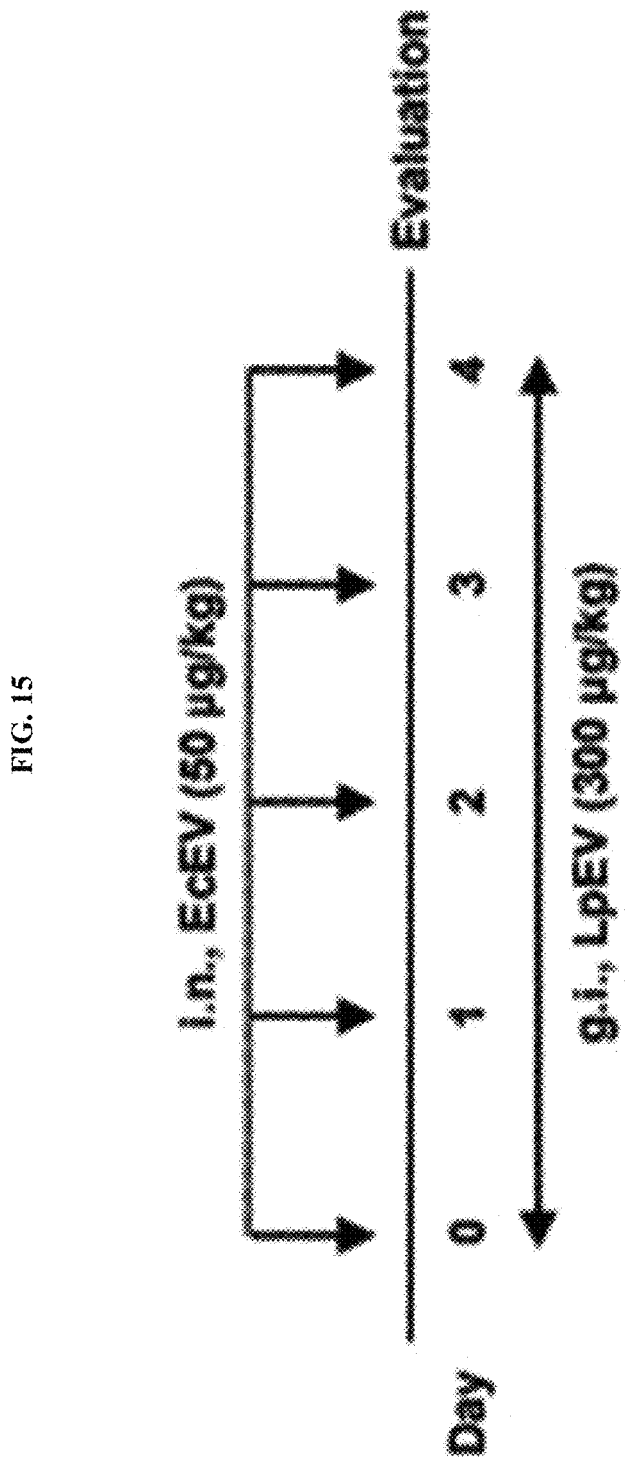
FIG. 15 illustrates an experimental method for evaluating the treatment effect of vesicles derived from *Lactobacillus paracasei* in a bacterial pneumonia mouse model.

Treatment Effect of Vesicles Derived from *Lactobacillus paracasei* in Bacterial Pneumonia Mouse Model In order to evaluate the treatment efficacy of vesicles derived from *Lactobacillus paracasei* in a bacterial pneumonia mouse model, an experiment was performed as follows by the method specified in FIG. 15.

That is, after five 6-week-old female C57BL/6 mice were placed in each cage without discrimination and given an acclimation time of 2 days, bacterial pneumonia was induced by intranasally administering 50 μg/kg vesicles derived from *E. coli*, which is a bacterial causative factor causing pneumonia, five times at 24-hour intervals. Vesicles (300 μg/kg) derived from *Lactobacillus paracasei* were orally administered five times at 24-hour intervals simultaneously with the start of the test, using a sonde (load for oral administration).

According to the above method, a bronchoalveolar lavage fluid was secured by dissecting the mice 24 hours after the final administration of vesicles derived from *Lactobacillus paracasei*, and the composition and degree of infiltration of immune cells in the bronchoalveolar lavage fluid were analyzed, and the expression levels of TNF-α, which is an inflammatory cytokine, myeloperoxidase (MPO), which is a neutrophil activation marker, and neutrophil elastase (NE) were analyzed. The degree of pulmonary inflammation was analyzed by removing lung tissue, performing H&E staining, and observing the lung tissue.

Figure 16:
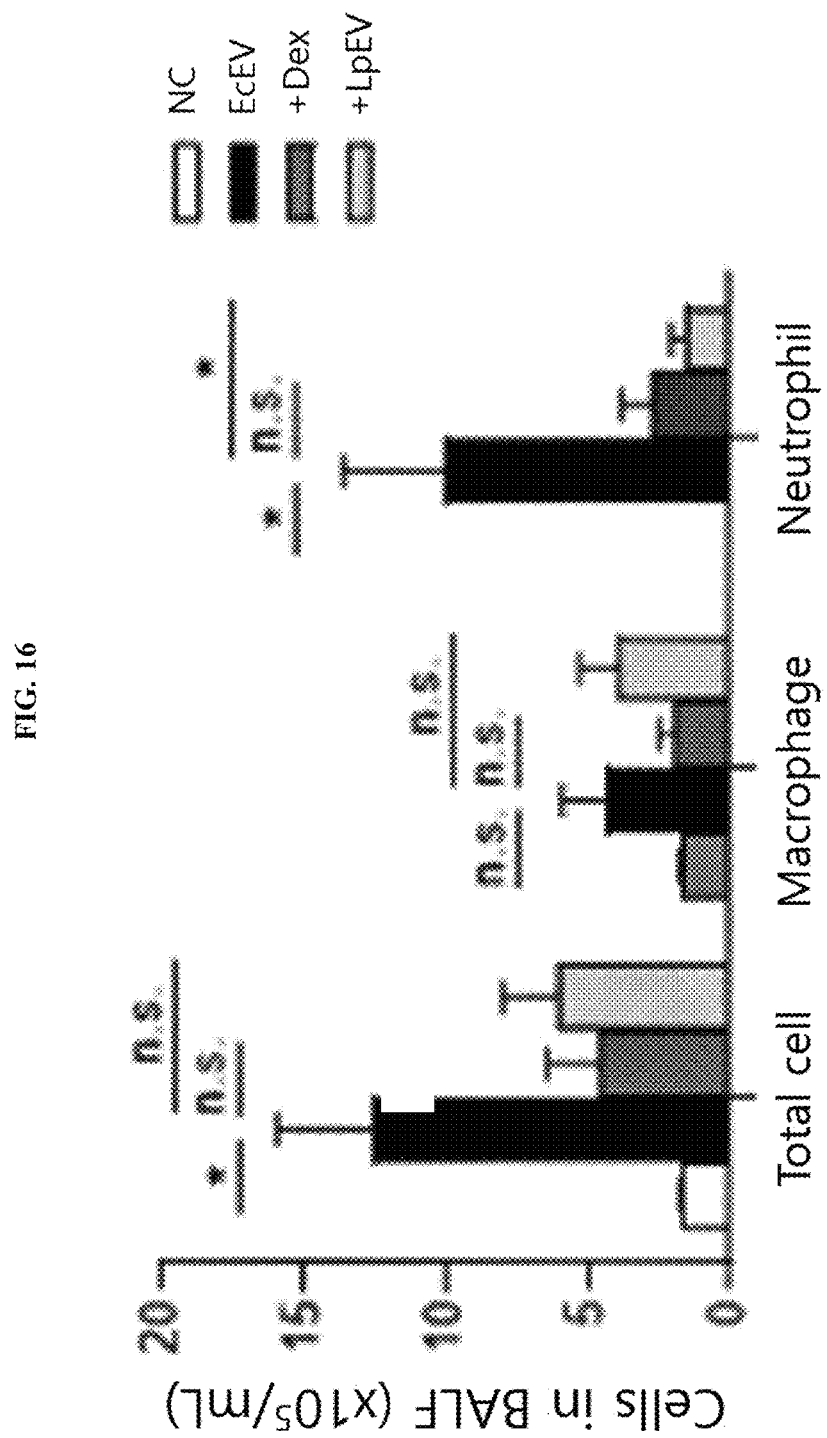
FIG. 16 illustrates the results of orally administering vesicles derived from *Lactobacillus paracasei* to a bacterial pneumonia mouse model and then evaluating the composition and number of inflammatory cells in a bronchoalveolar lavage fluid.

As a result, as illustrated in FIG. 16, it was confirmed that the number of total cells, the number of macrophages, and the number of neutrophils in a bronchoalveolar lavage fluid, which are indices from which the degree of pulmonary inflammation can be known, were remarkably decreased in the group to which vesicles derived from *Lactobacillus paracasei* compared to a positive control (EcEV), showing an effect similar to that of a group to which a control drug dexamethasone was administered.

Figure 17:
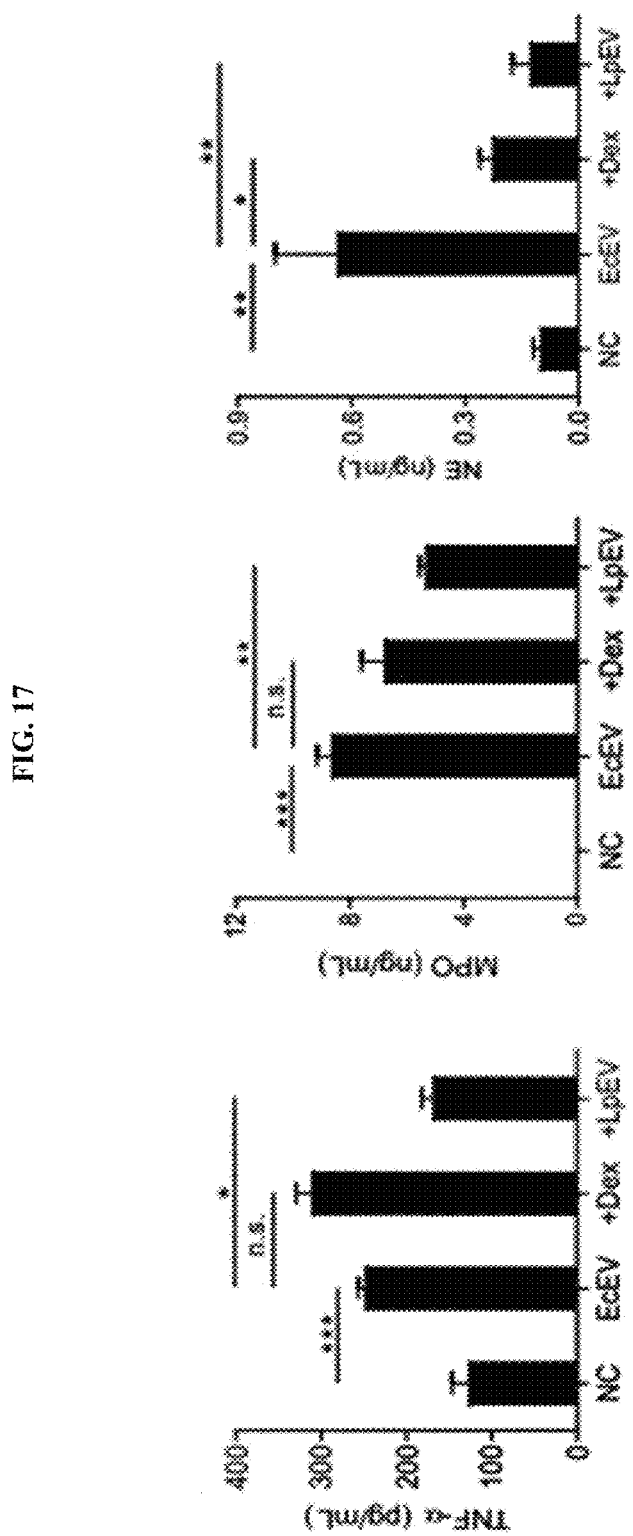
FIG. 17 illustrates the results of orally administering vesicles derived from *Lactobacillus paracasei* to a bacterial pneumonia mouse model and then quantifying the expression levels of TNF-α, which is an inflammatory cytokine, myeloperoxidase (MPO), which is a neutrophil activation marker, and neutrophil elastase (NE) in a bronchoalveolar lavage fluid by an ELISA method.
Figure 18:
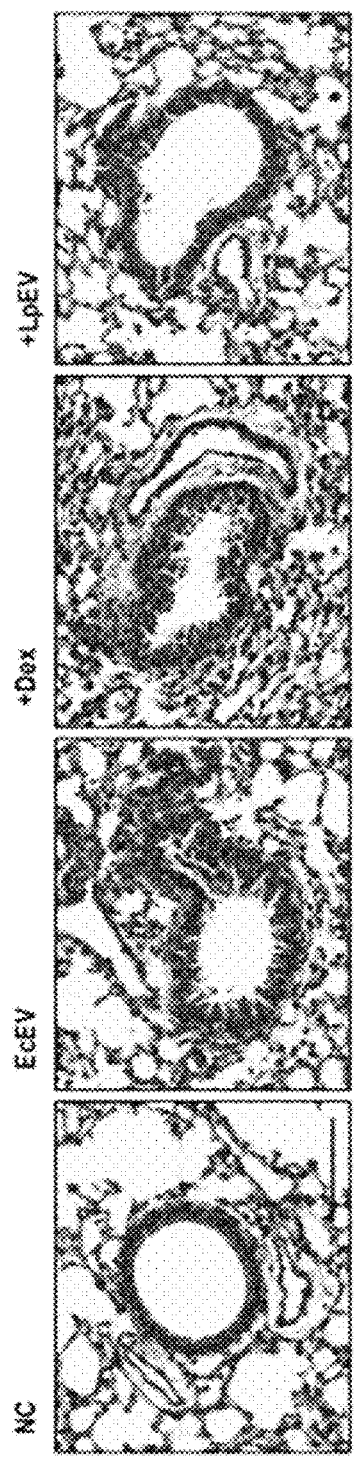
FIG. 18 illustrates the results of orally administering vesicles derived from *Lactobacillus paracasei* to a bacterial pneumonia mouse model and then evaluating the degree of infiltration of inflammatory cells by removing lung tissue and performing H&E staining on the lung tissue.

Furthermore, as illustrated in FIG. 17, it was confirmed that the expression levels of TNF-α, which is an inflammatory cytokine, MPO, which is a neutrophil activation marker, and NE in a bronchoalveolar lavage fluid, were also decreased compared to the positive control, and as illustrated in FIG. 18, it was confirmed that the infiltration of inflammatory cells into lung tissue was also reduced in the group to which vesicles derived from *Lactobacillus paracasei* were administered compared to the positive control.

The results as described above mean that vesicles derived from *Lactobacillus paracasei* efficiently suppress the occurrence of pneumonia caused by bacterial causative factors.

Example 7

Figure 19:
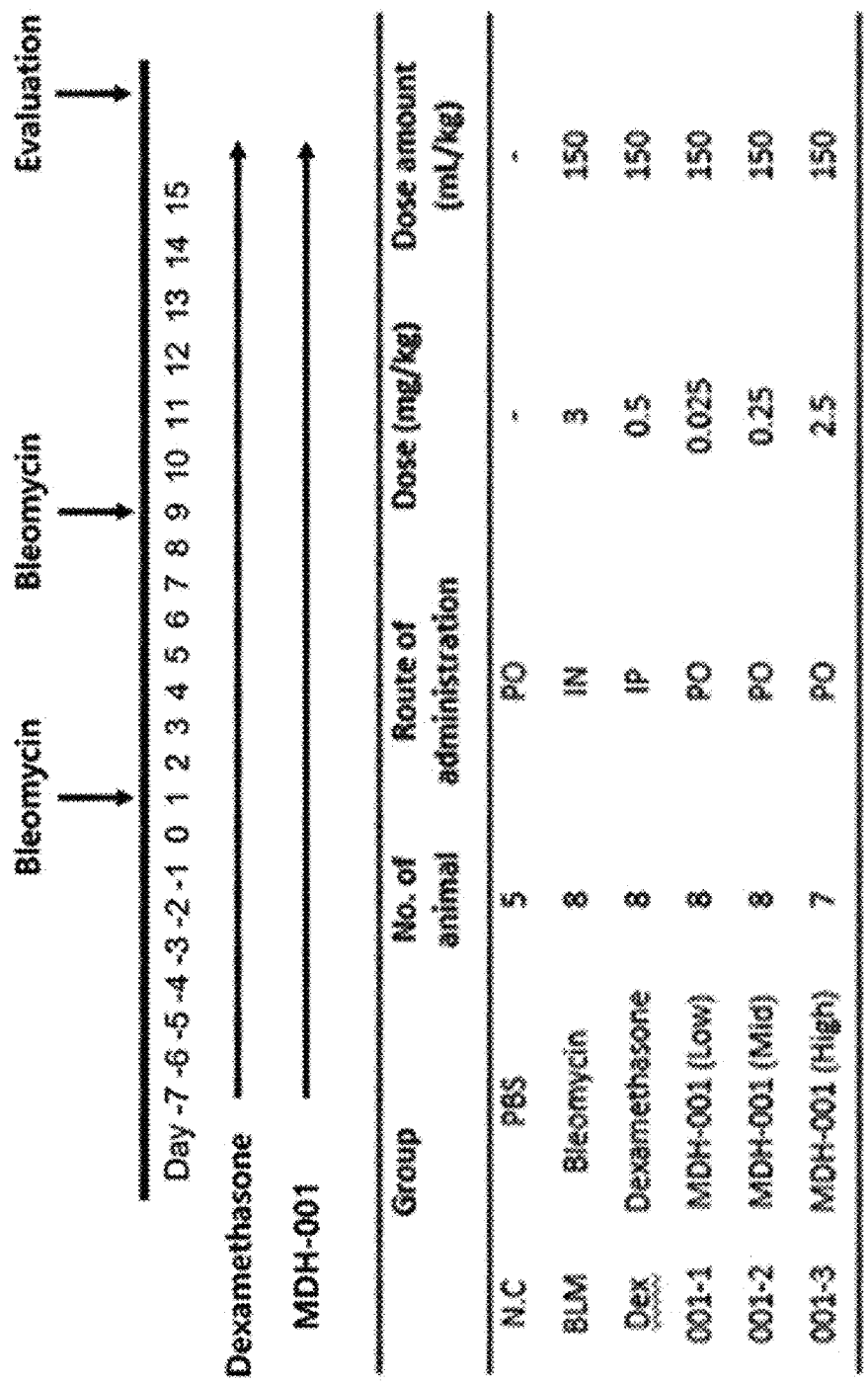
FIG. 19 illustrates an experimental method for evaluating the treatment effect of vesicles derived from *Lactobacillus paracasei* in an idiopathic pulmonary fibrosis mouse model induced by chemical factors.

Treatment Effect of Vesicles Derived from *Lactobacillus paracasei* in Mouse Model of Idiopathic Pulmonary Fibrosis Caused by Bleomycin In order to evaluate the treatment efficacy of vesicles derived from *Lactobacillus paracasei* in a mouse model of idiopathic pulmonary fibrosis caused by Bleomycin, an experiment was performed as follows by the method specified in FIG. 19.

That is, after five 6-week-old male C57BL/6 mice were placed in each cage without discrimination and given an acclimation time of 7 days, pulmonary fibrosis was induced by intranasally administering 3 mg/kg Bleomycin, which is a causative factor causing pulmonary fibrosis, twice at 8-day intervals. Vesicles derived from *Lactobacillus paracasei* (MDH-001-1: 0.025 mg/kg, MDH-001-2: 0.25 mg/kg, and MDH-001-3: 2.5 mg/kg) were orally administered three times at 48-hour intervals before the start of the test using a sonde (load for oral administration), and administered daily from the time of administration of Bleomycin.

According to the above method, a bronchoalveolar lavage fluid was secured by dissecting the mice 24 hours after the final administration of vesicles derived from *Lactobacillus paracasei*, and the number of neutrophils, which are representative inflammatory cells, in the bronchoalveolar lavage fluid was analyzed. Western blotting was performed on lung tissue to measure the difference in expression levels of α-smooth muscle actin (α-SMA) and phospho-SMAD family member 3 (p-smad3), which are important indices in the fibrosis process, and pulmonary inflammation and the degree of fibrosis were analyzed by removing some lung tissue and staining the lung tissue with H&E and Masson's trichrome.

Figure 20:
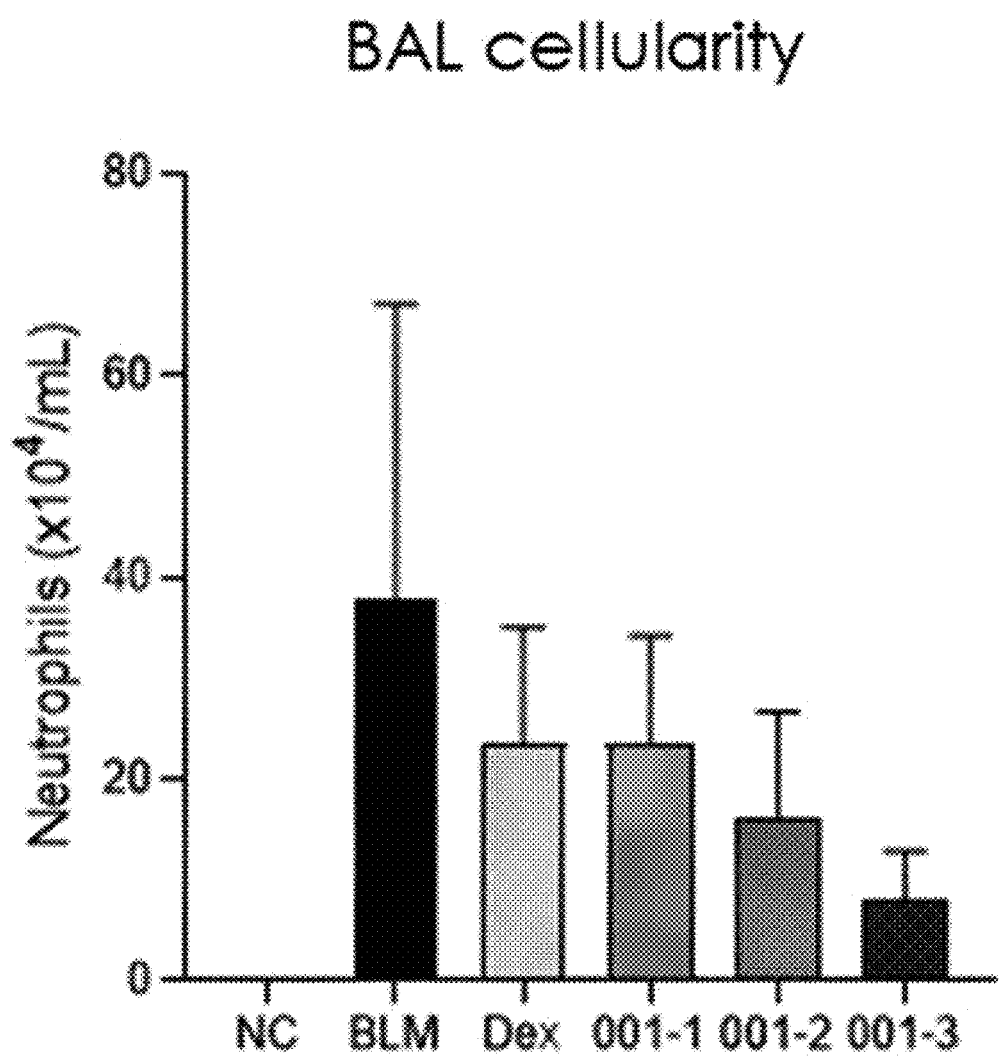
FIG. 20 illustrates the results of orally administering vesicles derived from *Lactobacillus paracasei* to an idiopathic pulmonary fibrosis mouse model and then evaluating the number of neutrophils, which are representative inflammatory cells, in a bronchoalveolar lavage fluid.

As a result, as illustrated in FIG. 20, it was confirmed that the number of neutrophils in a bronchoalveolar lavage fluid, which is an index from which the degree of pulmonary inflammation can be known, was decreased in a dose-dependent manner in a group to which the vesicles derived from *Lactobacillus paracasei* were administered compared to a positive control (BLM), and that the scope of decrease in the high-concentration administration group (MDH-001-3) was large compared to a group to which a control drug dexamethasone (Dex) was administered.

Figure 21:
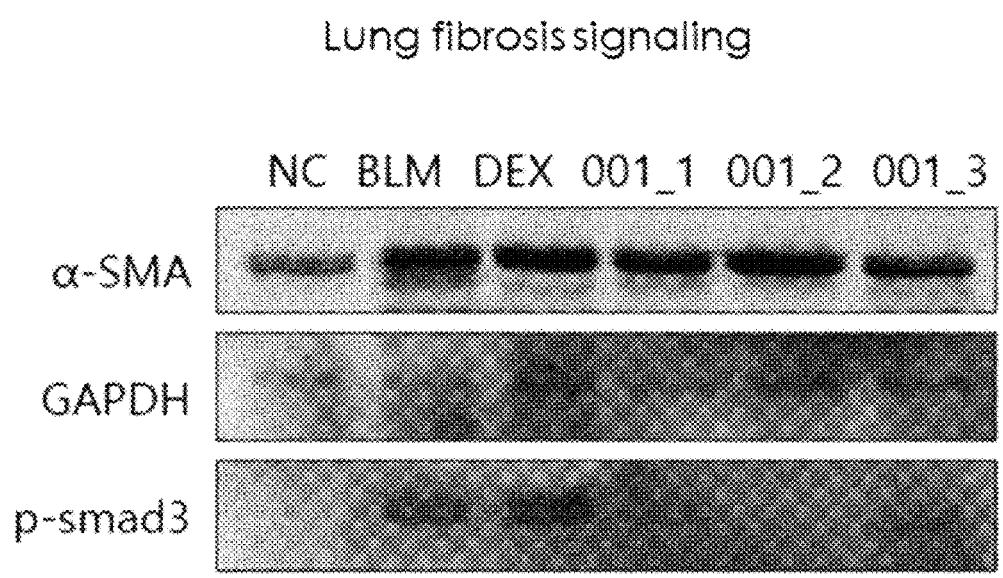
FIG. 21 illustrates the results of orally administering vesicles derived from *Lactobacillus paracasei* to an idiopathic pulmonary fibrosis mouse model and then quantifying the expression pattern of fibrosis-associated proteins in lung tissue using Western blot.

In addition, as illustrated in FIG. 21, as a result of analyzing the expression levels of α-SMA and p-smad3, which are important indices in the fibrosis process, it was confirmed that α-SMA tended to be decreased in a group to which a high concentration of vesicles derived from *Lactobacillus paracasei* was administered (MDH-001-3), and that the expression of p-smad3, which is a core signal of fibrosis, was reduced in the groups to which all concentrations of vesicles derived from *Lactobacillus paracasei* were administered.

Figure 22:
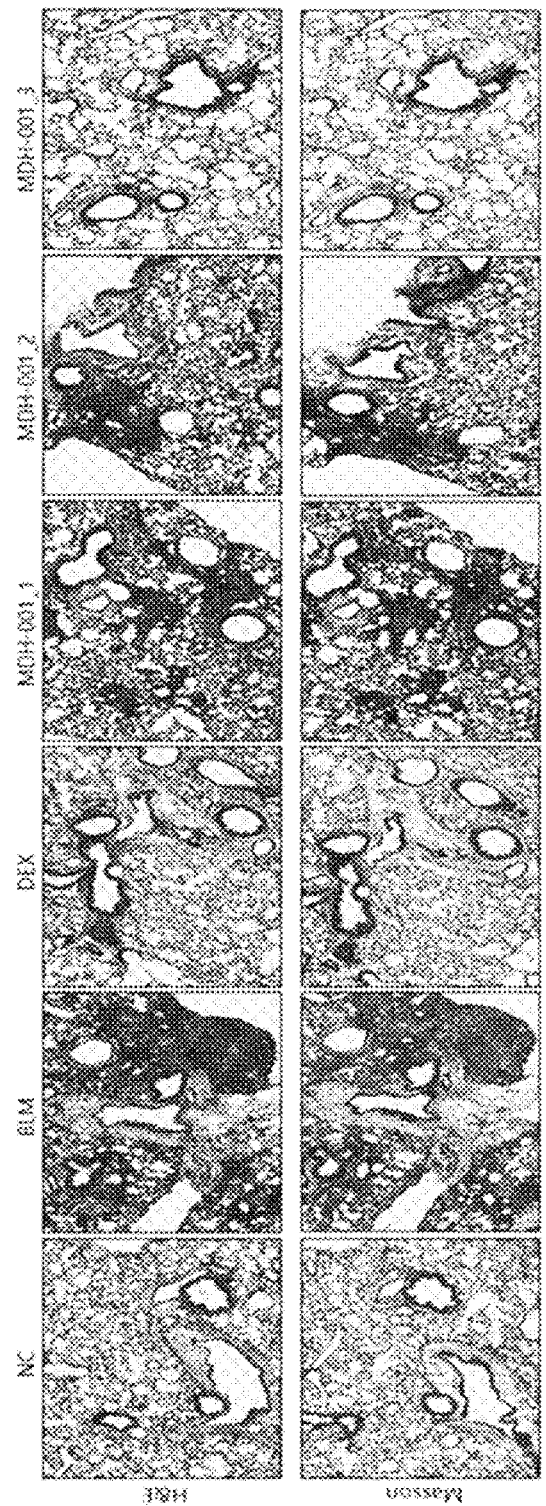
FIG. 22 illustrates the results of orally administering vesicles derived from *Lactobacillus paracasei* to an idiopathic pulmonary fibrosis mouse model and then evaluating the degree of infiltration of inflammatory cells by removing lung tissue and performing H&E staining on the lung tissue.

Furthermore, as illustrated in FIG. 22, as a result of observing lung histological changes by H&E and Masson's trichrome, it was confirmed that the infiltration of inflammatory cells and the deposition of collagen fibers were reduced in the group to which the vesicles derived from *Lactobacillus paracasei* were administered compared to the positive control.

Through the results described above, it could be seen that the vesicles derived from *Lactobacillus paracasei* effectively suppressed the occurrence of idiopathic pulmonary fibrosis caused by Bleomycin, which is a chemical causative factor.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The vesicles derived from *Lactobacillus paracasei* according to the present invention can be usefully used as a composition for preventing, alleviating, or treating a viral infectious disease or a respiratory disease, and thus have industrial applicability.

The invention claimed is:

1. A method for alleviating or treating a respiratory disease, the method comprising administering a composition comprising vesicles secreted by *Lactobacillus paracasei* as an active ingredient to a subject in need thereof,
wherein the vesicles are naturally secreted from *Lactobacillus paracasei*, or isolated from a culture solution of *Lactobacillus paracasei* or food prepared by adding *Lactobacillus paracasei*.

2. The method of claim 1, wherein the respiratory disease is any one or more selected from the group consisting of acute rhinitis, chronic rhinitis, acute sinusitis, chronic sinusitis, dysosmia, acute bronchitis, chronic bronchitis, acute bronchiolitis, chronic bronchiolitis, viral pneumonia, bacterial pneumonia, interstitial pneumonitis, vascular pneumonia, and idiopathic pulmonary fibrosis.

3. The method of claim 1, wherein the vesicles have an average diameter of 10 to 300 nm.

4. The method of claim 1, wherein the composition is a pharmaceutical composition, a food composition, or a cosmetic composition.

5. The method of claim 1, wherein the composition is an inhalant composition.

* * * * *